US012806276B2

(12) United States Patent
Haggarty et al.

(10) Patent No.: US 12,806,276 B2
(45) Date of Patent: Nov. 24, 2026

(54) INHIBITORS OF TTBK1

(71) Applicants: The General Hospital Corporation, Boston, MA (US); Dana-Farber Cancer Institute, Inc., Boston, MA (US)

(72) Inventors: Stephen John Haggarty, Gloucester, MA (US); Maria Catarina Telo Baptista Lima Da Silva, Revere, MA (US); Fleur Marcia Ferguson, Boston, MA (US); Nathanael S. Gray, Boston, MA (US)

(73) Assignees: The General Hospital Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 367 days.

(21) Appl. No.: 18/566,929

(22) PCT Filed: Jun. 7, 2022

(86) PCT No.: PCT/US2022/072793
§ 371 (c)(1),
(2) Date: Dec. 4, 2023

(87) PCT Pub. No.: WO2022/261627
PCT Pub. Date: Dec. 15, 2022

(65) Prior Publication Data
US 2024/0285777 A1 Aug. 29, 2024

Related U.S. Application Data

(60) Provisional application No. 63/197,809, filed on Jun. 7, 2021.

(51) Int. Cl.
*A61K 47/55* (2017.01)
*A61K 47/54* (2017.01)
*A61P 25/28* (2006.01)

(52) U.S. Cl.
CPC ........... *A61K 47/55* (2017.08); *A61K 47/542* (2017.08); *A61P 25/28* (2018.01)

(58) Field of Classification Search
CPC .... A61K 47/55; A61K 47/542; A61K 31/192; A61P 25/28; C07D 487/04
See application file for complete search history.

(56) References Cited

U.S. PATENT DOCUMENTS

| | | | |
|---|---|---|---|
| 5,304,121 | A | 4/1994 | Sahatjian |
| 5,886,026 | A | 3/1999 | Hunter et al. |
| 6,099,562 | A | 8/2000 | Ding et al. |
| 6,803,031 | B2 | 10/2004 | Rabinowitz et al. |
| 2018/0179183 | A1 | 6/2018 | Crew et al. |
| 2019/0016703 | A1 | 1/2019 | Gray et al. |
| 2020/0347068 | A1 | 11/2020 | Gray et al. |
| 2021/0154184 | A1* | 5/2021 | Gray .................. A61K 31/4545 |

FOREIGN PATENT DOCUMENTS

| | | | |
|---|---|---|---|
| JP | 2018-531983 | A | 11/2018 |
| JP | 2020-527559 | A | 9/2020 |
| WO | WO 2018/119441 | | 6/2018 |
| WO | WO 2019/114770 | | 6/2019 |

OTHER PUBLICATIONS

International Preliminary Report on Patentability in International Appln. No. PCT/US2022/072793, mailed Dec. 21, 2023, 7 pages.
Asai et al., "Accelerated Neurodegeneration and Neuroinflammation in Transgenic Mice Expressing P301L Tau Mutant and Tau-Tubulin Kinase 1," Am J Pathol., Mar. 2014, 184(3):808-18.
Dillon et al., "Acute inhibition of the CNS-specific kinase TTBK1 significantly lowers tau phosphorylation at several disease relevant sites," PLoS One, Apr. 2020, 15(4):e0228771, 22 pages.
Groppe, "Induced degradation of protein kinases by bifunctional small molecules: a next-generation strategy," Expert Opinion on Drug Discovery, Aug. 2019, 14(12):1237-1253.
Illum, "Is nose-to-brain transport of drugs in man a reality?," J Pharm Pharmacol, Jan. 2004, 56(1):3-17.
Illum, "Transport of drugs from the nasal cavity to the central nervous system," Eur J Pharm Sci., Jul. 2000, 11(1):1-18.
International Search Report & Written Opinion in International Appln. No. PCT/US2022/072793, mailed Sep. 9, 2022, 9 pages.
Liachko et al., "The Tau Tubulin Kinases TTBK1/2 Promote Accumulation of Pathological TDP-43," PLoS Genet., Dec. 2014, 10(12):e1004803, 14 pages.
Lund et al., "Tau-Tubulin Kinase 1 Expression, Phosphorylation and Co-Localization with Phospho-Ser422 Tau in the Alzheimer's Disease Brain," Brain Pathology, Jul. 2013, 23(4):378-389.
Nozal and Martinez, "Tau Tubulin Kinase 1 (TTBK1), a new player in the fight against neurodegenerative diseases," Eur J Med Chem., Jan. 2019, 161:39-47.
Sato et al., "Spatial learning impairment, enhanced CDK5/p35 activity, and downregulation of NMDA receptor expression in transgenic mice expressing tau-tubulin kinase 1," J Neurosci., Dec. 2008, 28(53):14511-21.
Sato et al., "Tau-tubulin kinase 1 (TTBK1), a neuron-specific tau kinase candidate, is involved in tau phosphorylation and aggregation," J Neurochem, Sep. 2006, 98(5):1573-84.

(Continued)

*Primary Examiner* — Rebecca L Anderson
*Assistant Examiner* — David M Shim
(74) *Attorney, Agent, or Firm* — Fish & Richardson P.C.

(57) ABSTRACT

The present application provides a compound of Formula (I) as described herein, or a pharmaceutically acceptable salt thereof. Pharmaceutical compositions comprising the compound of Formula (I), and methods of using said compound and said compositions for treating neurodegenerative diseases, are also provided.

22 Claims, 12 Drawing Sheets

(56) References Cited

OTHER PUBLICATIONS

Seo et al., “Inhibition of p25/Cdk5 Attenuates Tauopathy in Mouse and iPSC Models of Frontotemporal Dementia,” J Neurosci., Oct. 2017, 37(41):9917-9924.
Sheridan et al., “Epigenetic characterization of the FMR1 gene and aberrant neurodevelopment in human induced pluripotent stem cell models of fragile X syndrome,” PLoS One, 2011, 6(10):e26203, 13 pages.
Silva et al., “Human iPSC-Derived Neuronal Model of Tau-A152T Frontotemporal Dementia Reveals Tau-Mediated Mechanisms of Neuronal Vulnerability,” Stem Cell Reports, Sep. 2016, 7(3):325-340.
Silva et al., “Targeted degradation of aberrant tau in frontotemporal dementia patient-derived neuronal cell models,” eLife, Mar. 2019, 8:e45457, 31 pages.
Taylor et al., “Pathological phosphorylation of tau and TDP-43 by TTBK1 and TTBK2 drives neurodegeneration,” Mol Neurodeg, Feb. 2018, 13(1):7, 14 pages.
Taylor et al., “Tau tubulin kinases in proteinopathy,” FEBS J., Jul. 2019, 286(13):2434-2446.
Xu et al., “Tau-tubulin kinase 1 enhances prefibrillar tau aggregation and motor neuron degeneration in P301L FTDP-17 tau-mutant mice,” FASEB J., Aug. 2010, 24(8):2904-15.
Xue et al., “X-ray Structural Analysis of Tau-Tubulin Kinase 1 and Its Interactions with Small Molecular Inhibitors,” ChemMedChem, Nov. 2013, 8(11):1846-1854.
Notice of Intention to Grant in European Appln. No. 22821235.3, mailed on Nov. 14, 2025, 8 pages.
Extended European Search Report in European Appln. No. 22821235.3, mailed on Mar. 3, 2025, 8 pages.
Office Action in Japanese Appln. No. 2023-575408, mailed Jan. 27, 2026, 8 pages.
Ohoka et al., “Drug discovery modality of new small molecule drugs PROTAC Development History and Latest Trends,” Pharmacia. 2020, 56(1):41-45 (with English translation).
Yuka et al., “Development and Advances of PROTACs: Induced Protein Degradation by Hijacking Ubiquitin Ligase,” Journal of Synthetic Organic Chemistry, Apr. 2018, 76(4):358-359 (with English abstract).

* cited by examiner

Figure Adapted: Nozal & Martinez, 2019 *European Journal of Medicinal Chemistry*

INHIBITORS OF TTBK1

CLAIM OF PRIORITY

This application is the U.S. National Phase Application under 35 U.S.C. § 371 of International Patent Application No. PCT/US2022/072793, filed on Jun. 7, 2022, which claims the benefit of U.S. Provisional Application Ser. No. 63/197,809 filed on Jun. 7, 2021. The entire contents of the foregoing are incorporated herein by reference in their entireties.

TECHNICAL FIELD

The present disclosure relates to thalidomide-based compounds that degrade tau tubulin kinase 1 (TTBK1), and methods of use thereof for treating tau pathologies and thus Alzheimer's disease and related tauopathies.

BACKGROUND

There are numerous deadly diseases affecting current human population. For example, neurodegenerative diseases affect a significant segment of population, especially the elderly. Alzheimer's disease ("AD") and related tauopathies are neurodegenerative disorders that are the most common cause of dementia and the fifth leading cause of death in adults older than 65 years. Estimated annual socioeconomic burden of these disorders is over $300 billion.

TTBK1 is implicated in various neurodegenerative diseases. See, e.g., Nozal V, Martinez A. Tau Tubulin Kinase 1 (TTBK1), a new player in the fight against neurodegenerative diseases. Eur J Med Chem. 2019 Jan. 1; 161:39-47. doi: 10.1016/j.ejmech.2018.10.030. and Taylor L M, McMillan P J, Kraemer B C, Liachko N F. Tau tubulin kinases in proteinopathy. FEBS J. 2019 July; 286(13):2434-2446. doi: 10.1111/febs.14866. For example, increased TTBK1 expression has been observed in the brains of subjects with Alzheimer's disease and Frontotemporal lobar degeneration (FTLD). See, e.g., Sato, et al., J Neurosci. 2008 Dec. 31; 28(53):14511-21. doi: 10.1523/JNEUROSCI.3417-08.2008. TTBK1 transgenic mice also show elevated levels of tau phosphorylation, accelerated neurodegeneration, and enhanced neuroinflammation when crossed with P301L tau mice. See, e.g., Xu, et al., FASEB J. 2010 August; 24(8): 2904-15. doi: 10.1096/fj.09-150144. Moreover, silencing TTBK1 attenuates LPS-stimulated microglia-induced neurodegeneration. See, e.g., Asai et al. Am J Pathol. 2014 March; 184(3):808-18. doi: 10.1016/j.ajpath. 2013.11.026.

SUMMARY

In one general aspect, the present disclosure provides a compound of Formula (I):

(I)

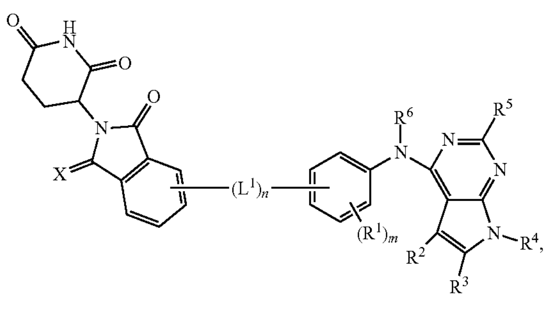

or a pharmaceutically acceptable salt thereof, wherein X, $L^1$, n, $R^1$, m, $R^2$, $R^3$, $R^4$, $R^5$, and $R^6$ are as described herein.

In another general aspect, the present disclosure provides a pharmaceutical composition comprising a compound of Formula (I), or a pharmaceutically acceptable salt thereof, and a pharmaceutically acceptable carrier.

In yet another general aspect, the present disclosure provides a method of treating a neurodegenerative disease or disorder selected from tauopathy, Alzheimer's disease, frontotemporal dementia, amyotrophic lateral sclerosis, multiple sclerosis, frontotemporal lobar degeneration with tau pathology, Huntington's disease, and Parkinson's disease, the method comprising administering to the subject in need thereof a therapeutically effective amount of a compound of Formula (I), or a pharmaceutically acceptable salt thereof, or a pharmaceutical composition comprising same.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

P-tau, both TTBK1-specific sites and in contrast has low-to-no effect on the S396 P-site.

Figure 1:
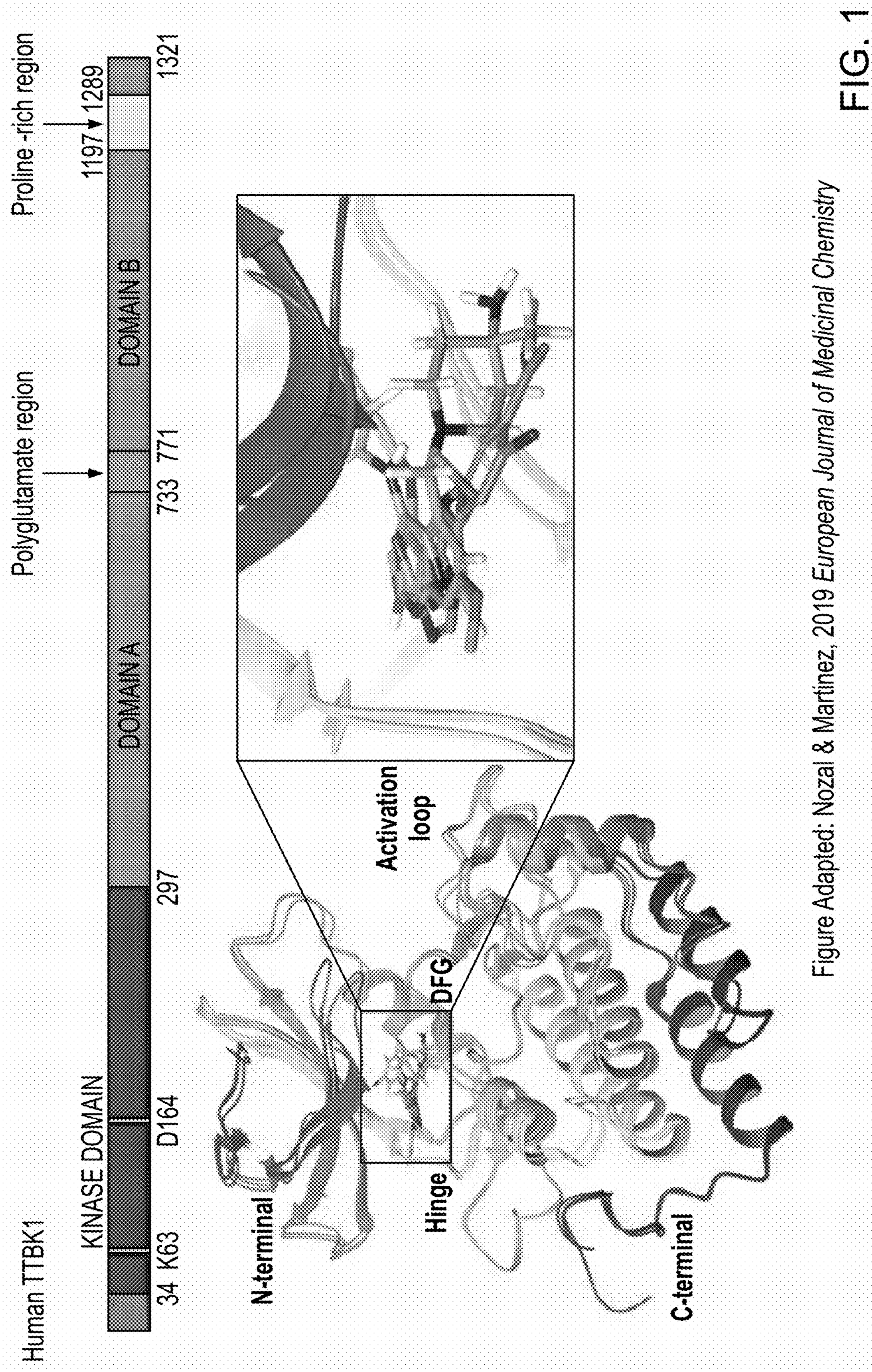
FIG. 1. Illustrates the structure of TTBK1.
Figure 2:
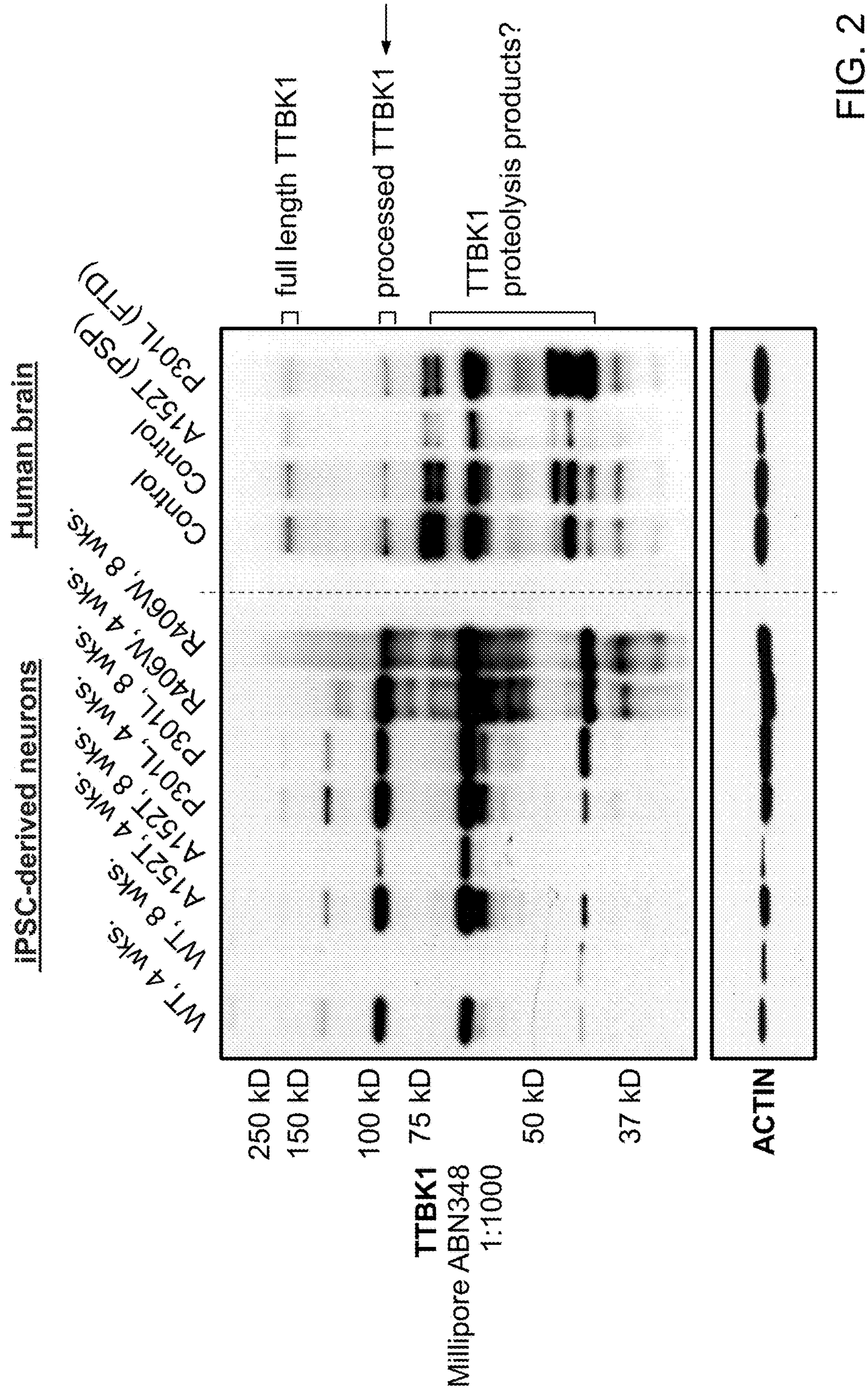
FIG. 2. Illustrates analysis of TTBK1 expression levels (Millipore ABN348 antibody for TTBK1) in post-mortem human brain tissue from control and tauopathy patient samples in comparison to human iPSC-derived neurons within the neural differentiation window of 4 or 8 weeks via western blot of total protein loaded. The full length TTBK1 (band at 150-200 kDa) was detected along with processed TTBK1 forms of lower molecular weight consistent with literature reports.
Figure 3:
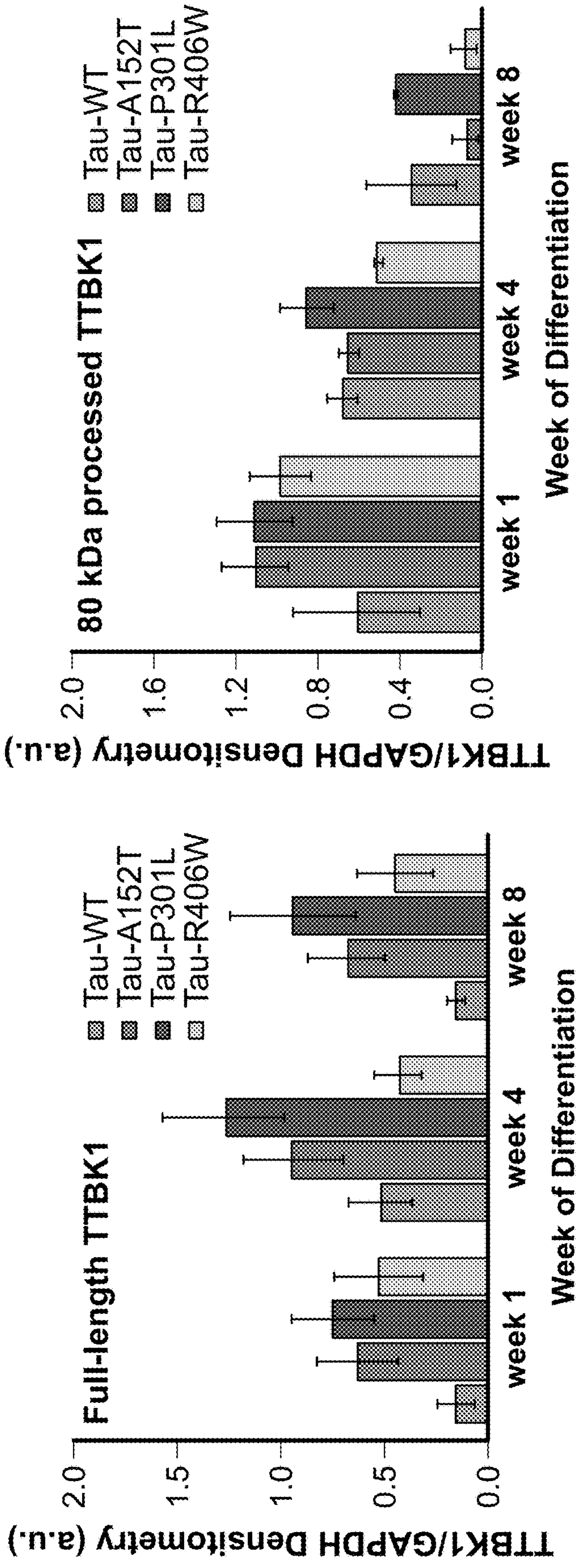
FIG. 3. Illustrates analysis of TTBK1 expression levels (Millipore ABN348 antibody for TTBK1) in human iPSC-derived neurons via western blot of total protein loaded and within the neural differentiation window of 1 to 8 week. For the full length TTBK1 (band at 150-200 kDa) there was a tendency for higher TTBK1 in the mutant neurons, but this was not statistically significant. For the predicted lysosomal-processed form of TTBK1 (80 kDa band) there was no tau mutation-dependent increase in TTBK1 protein, except at week 2 of neural differentiation.
Figure 4:
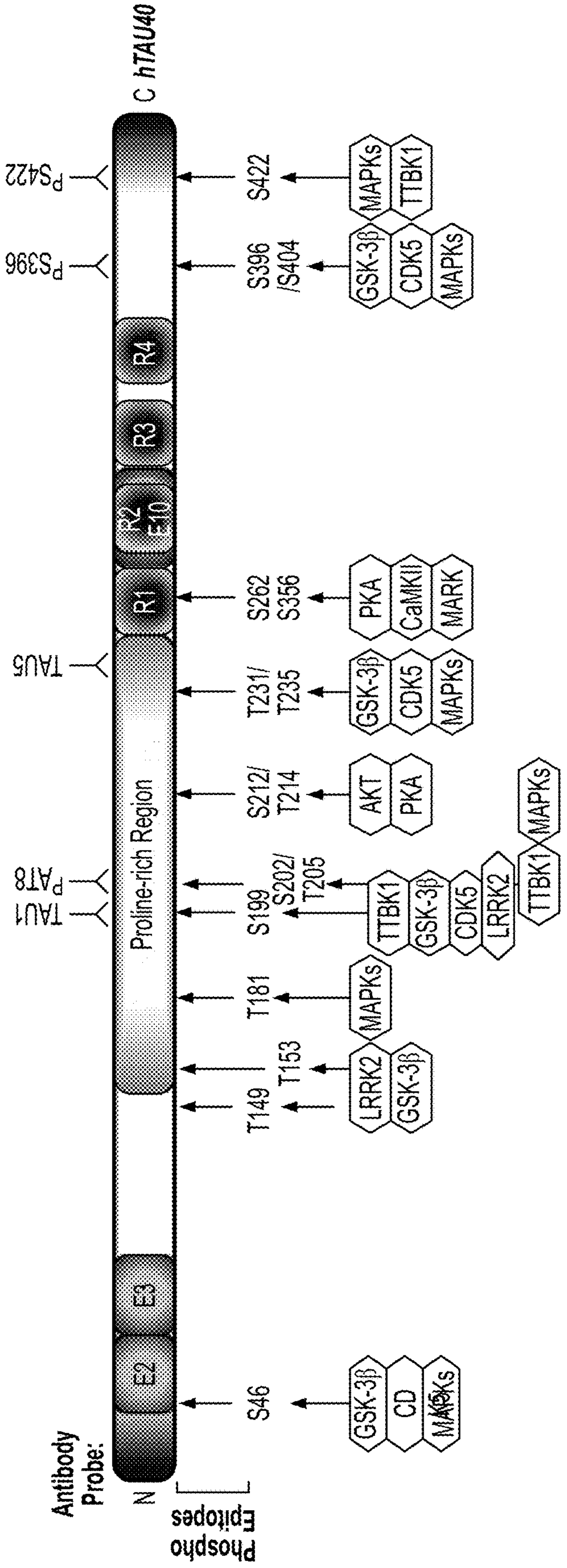
FIG. 4. Illustrates map of known tau phospho-epitopes, kinases associated with each site, and antibody probes appropriate for assaying the activity of cognate kinases. Sties known to be phosphorylated by TTBK1, including S199, 5202/T205 and S422 are known disease-relevant sites associated with tauopathy.
Figure 5:
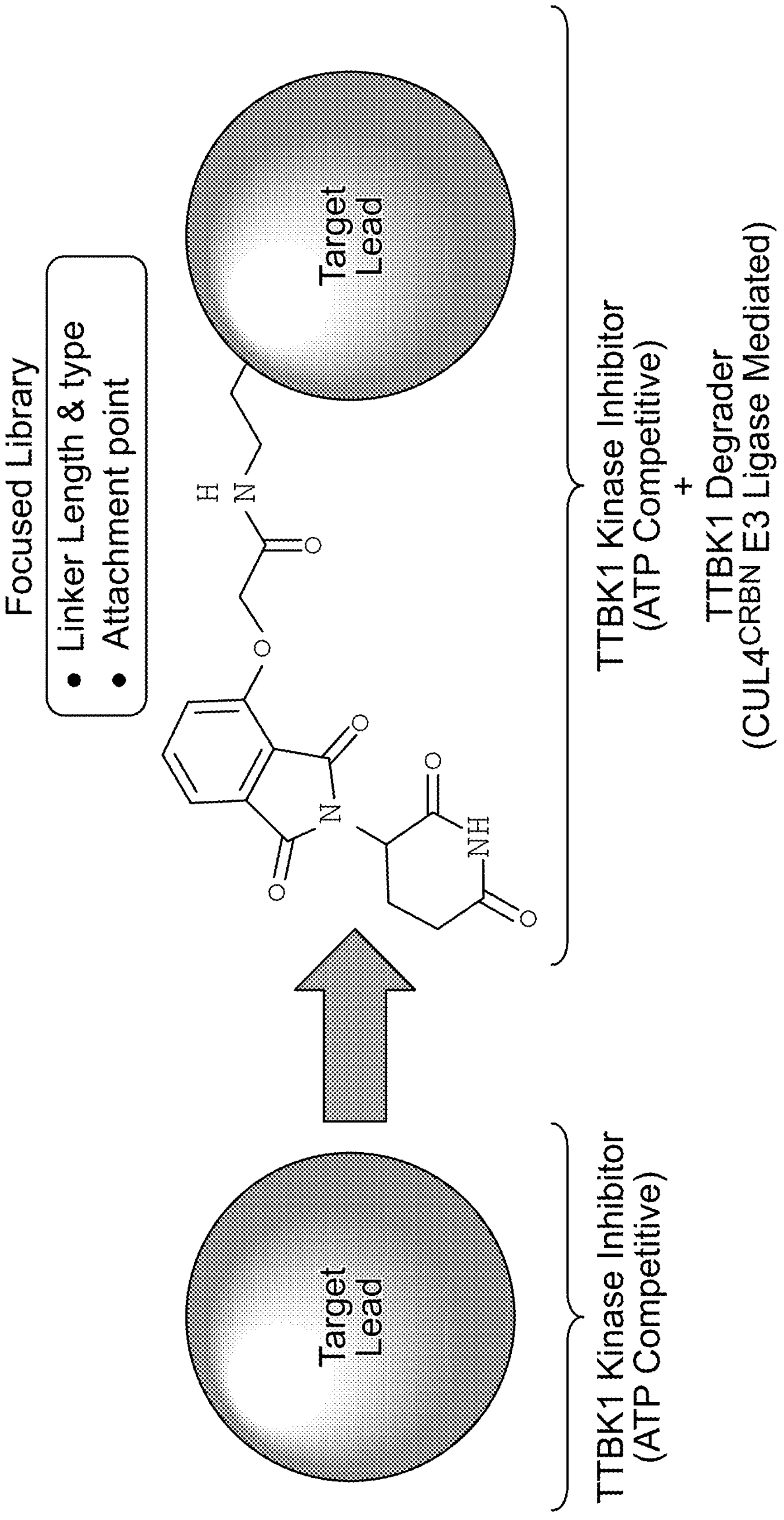
FIG. 5. Illustrates the design of first-generation "TTBK-IMiDs" for targeted degradation of tau-tubulin kinase 1.
Figure 6:
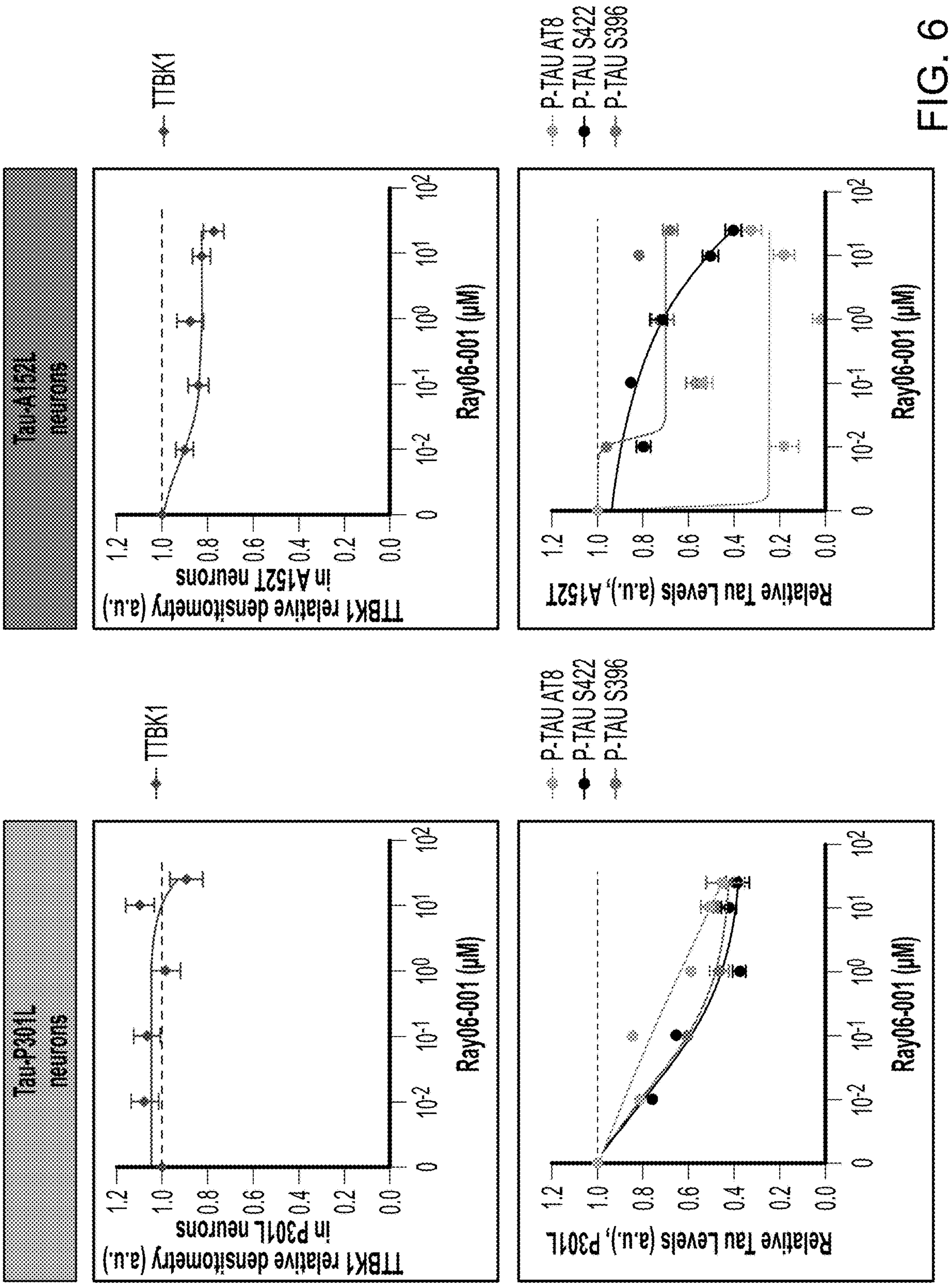
FIG. 6. Illustrates that RAY06-001 does not significantly affect steady-state levels of TTBK1 protein. However, the compound does result in a decrease in both AT8 and S422
Figure 7:
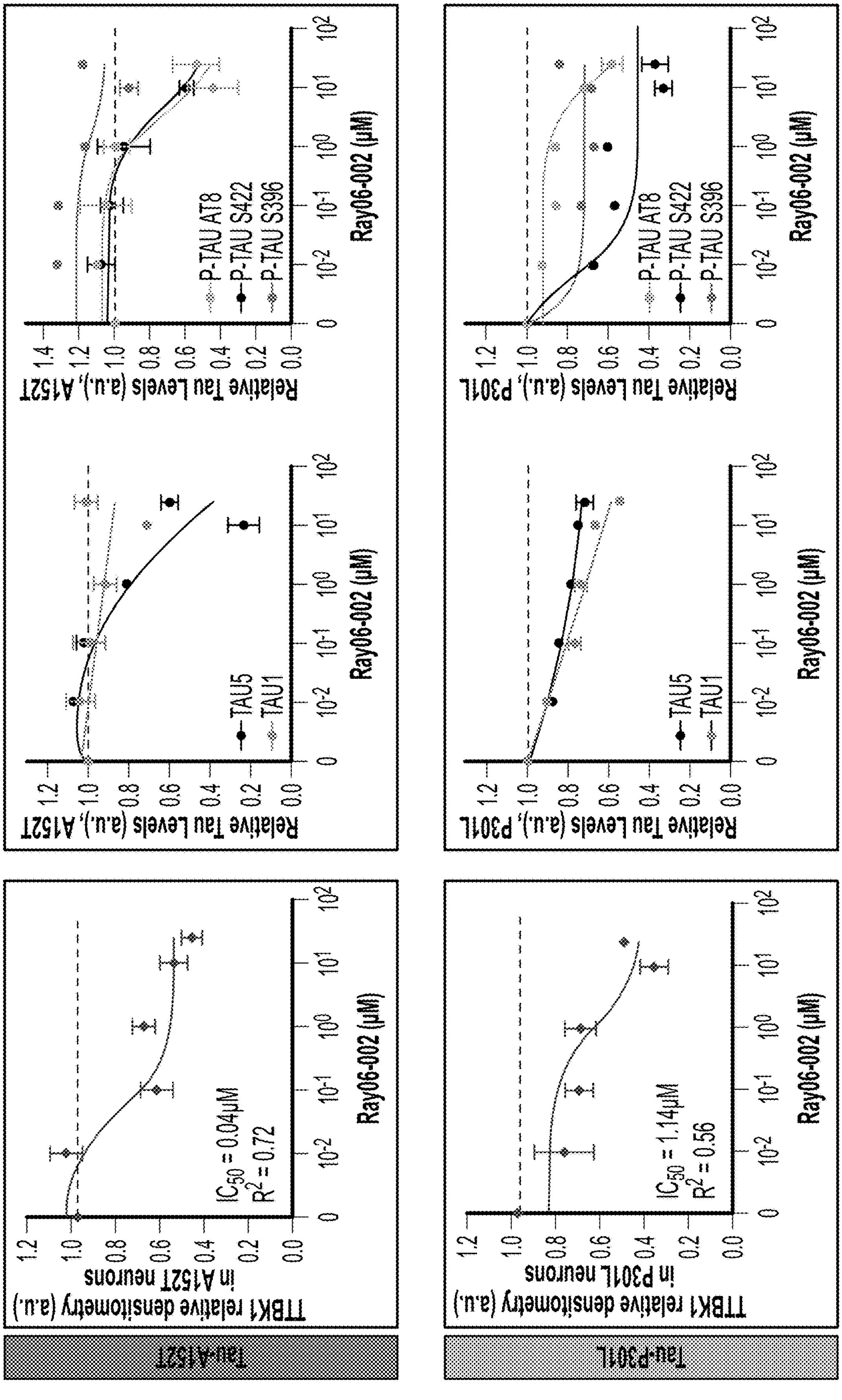

FIG. 7. Illustrates the effect of Ray06-002 is consistent with TTBK1 dose-dependent degradation. With reduced levels of TTBK1, there was also a reduction in total tau (TAU5) and P-tau AT8 and S422. The effect of this TTBK-IMiD on S396 P-tau is less significant, particularly in A152T neurons. When examining the P-tau/total tau ratio, an effect by Ray06-002 was only observed at the highest concentrations (P301L neurons), which suggests that reduction in P-tau at lower concentrations occurs in parallel to a reduction in total tau, possibly due to changes in tau oligomerization and degradation propensity. At higher doses, the reduction in tau phosphorylation becomes more accentuated than the process that leads to total tau reduction.

Figure 8:
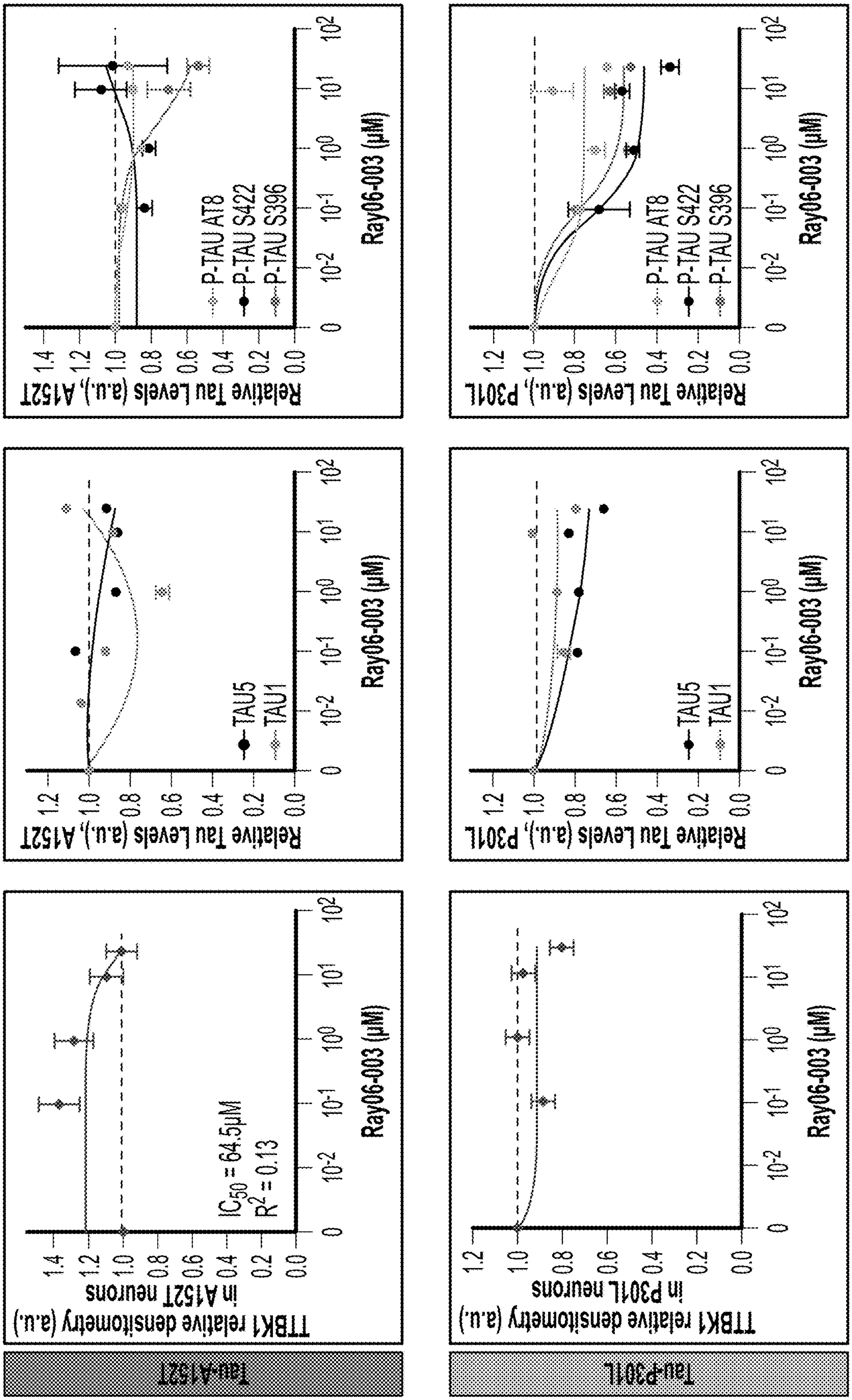

FIG. 8. Illustrates the TTBK1 degrader Ray06-003 does not appear to promote TTBK1 degradation, and therefore any effect seen on P-tau levels (and even total tau) should be due to the TTBK1 inhibitory effect retained by the molecule. However, the effect on P-tau is mainly/only seen in P301L neurons.

Figure 9:
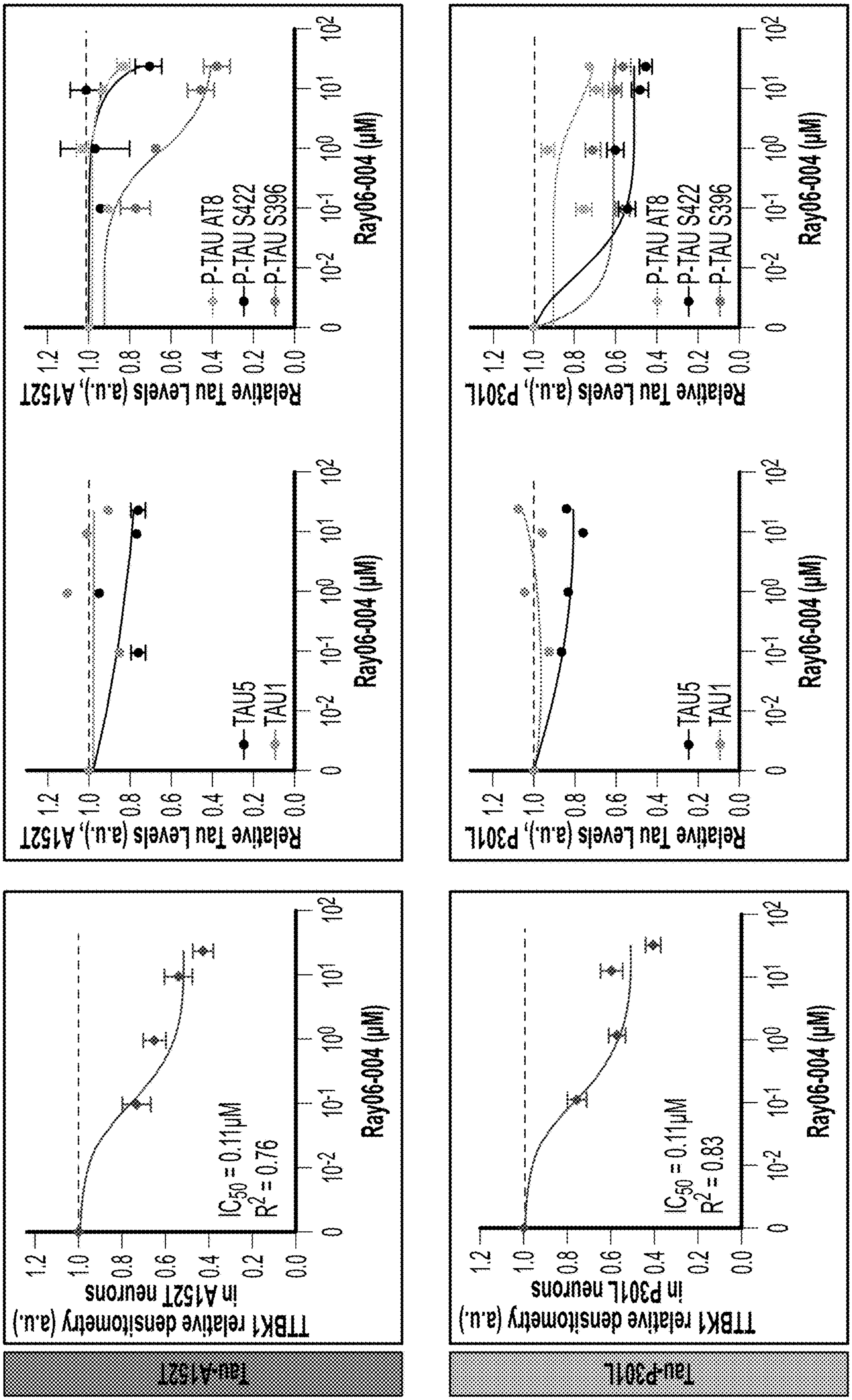

FIG. 9. Illustrates the effect of Ray06-004 was consistent with TTBK1 dose-dependent degradation to as low as 40% of basal levels and with the same $IC_{50}$ in both tauopathy neuron models. However, the effect of reduced TTBK1 on P-tau was only observed at the higher concentrations of compound (A152T neurons) or shows little dose-dependence (P301L neurons). Unexpectedly, with this degrader the effect on P-tau S396 was more accentuated than for P-tau AT8.

Figure 10:
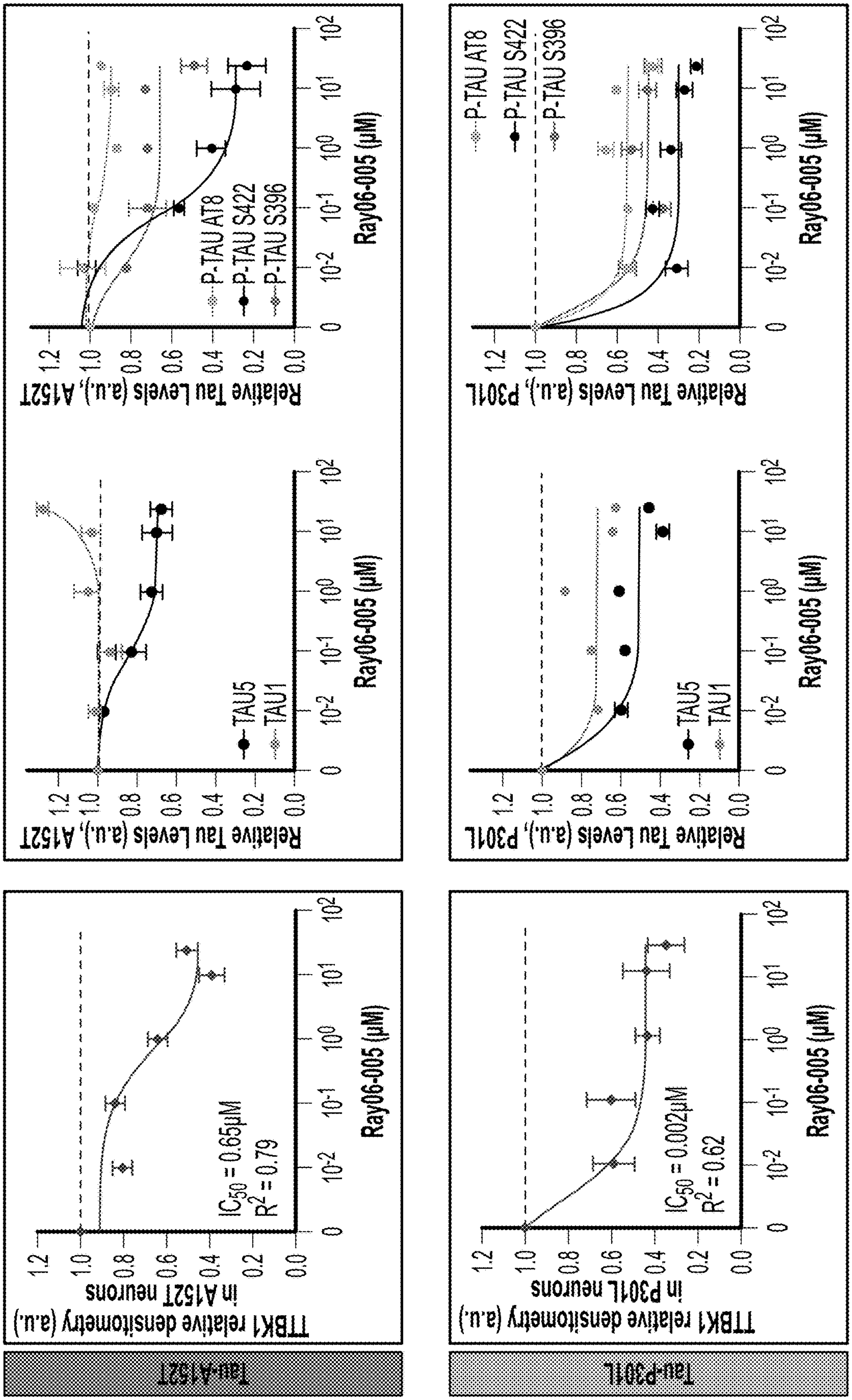

FIG. 10. Illustrates Ray06-005 reduced TTBK1 levels in a dose-dependent manner in both neuronal models. It also caused a reduction in total tau levels, particularly in the A152T model, where a dose-dependent effect is clearer (with some increase in the non-P-tau TAU1). With reduced levels of TTBK1, there was also a reduction in P-tau across all epitopes tested, whether TTBK1-dependent (AT8, S422) or not (S396). The most accentuated reduction was seen for P-tau S422. As for Ray06-002, the results suggest that reduction in P-tau occurs in parallel to a reduction in total tau, possibly due to changes in tau oligomerization and degradation propensity.

Figure 11:
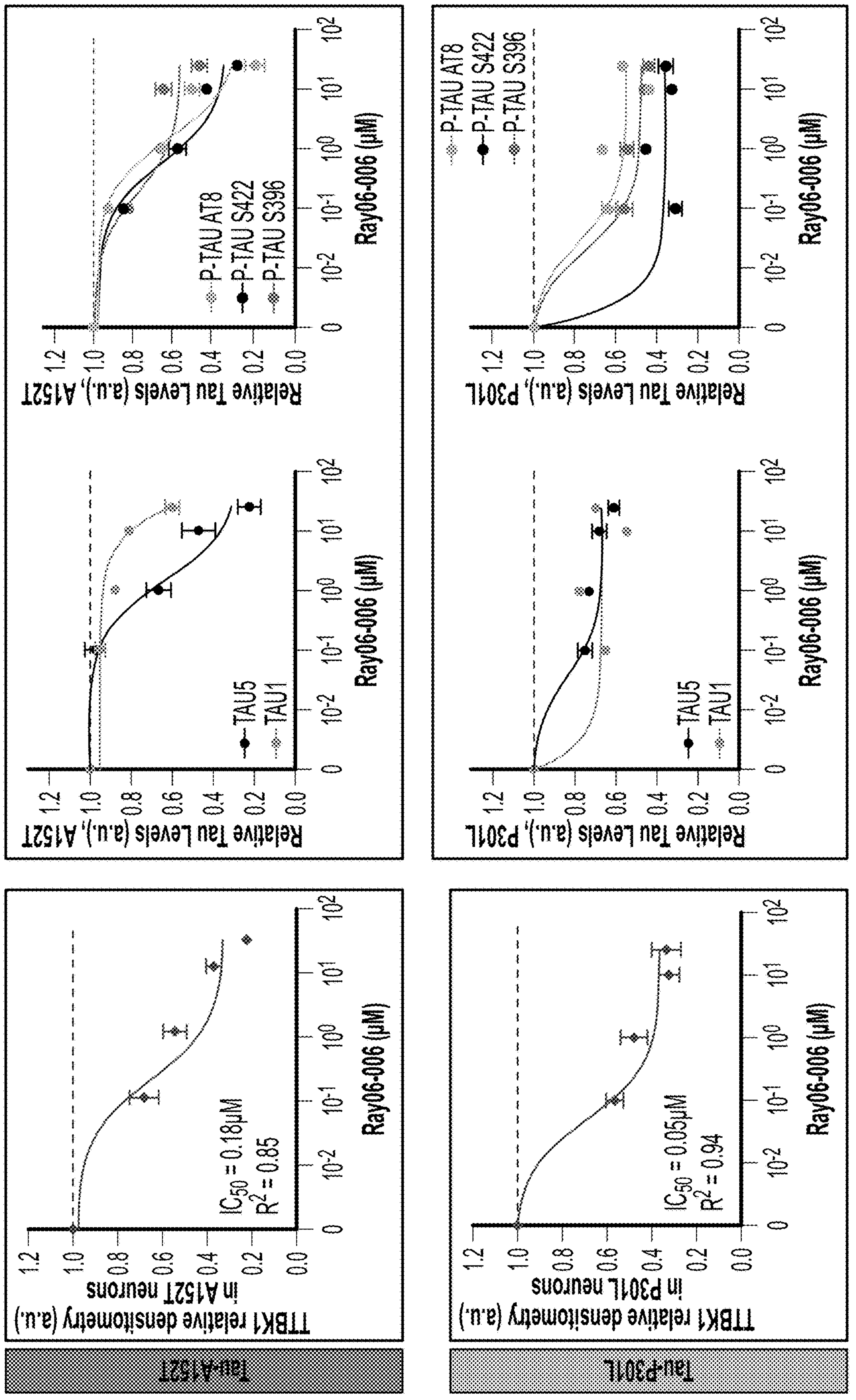

FIG. 11. Illustrates that Ray06-006 showed the strongest dose-dependent effect on TTBK1 protein levels with $IC_{50}$ of 0.05-0.2 μM. Regarding tau, a reduction in total tau was observed with a strong dose-dependent effect in the A152T model. There was also a reduction in P-tau across all epitopes tested, whether TTBK1-dependent (AT8, S422) or not (S396). The results suggest that reduction in P-tau occur in parallel to a reduction in total tau, possibly due to changes in tau oligomerization and degradation propensity. Analysis of P-tau/total tau in A152T suggests that the reduction in tau phosphorylation and in total tau levels were very similar, except for S396 P-tau (non-TTBK1 site). For the P301L neurons, reduction in tau phosphorylation seems to be even more accentuated that the effect on total tau.

Figure 12:
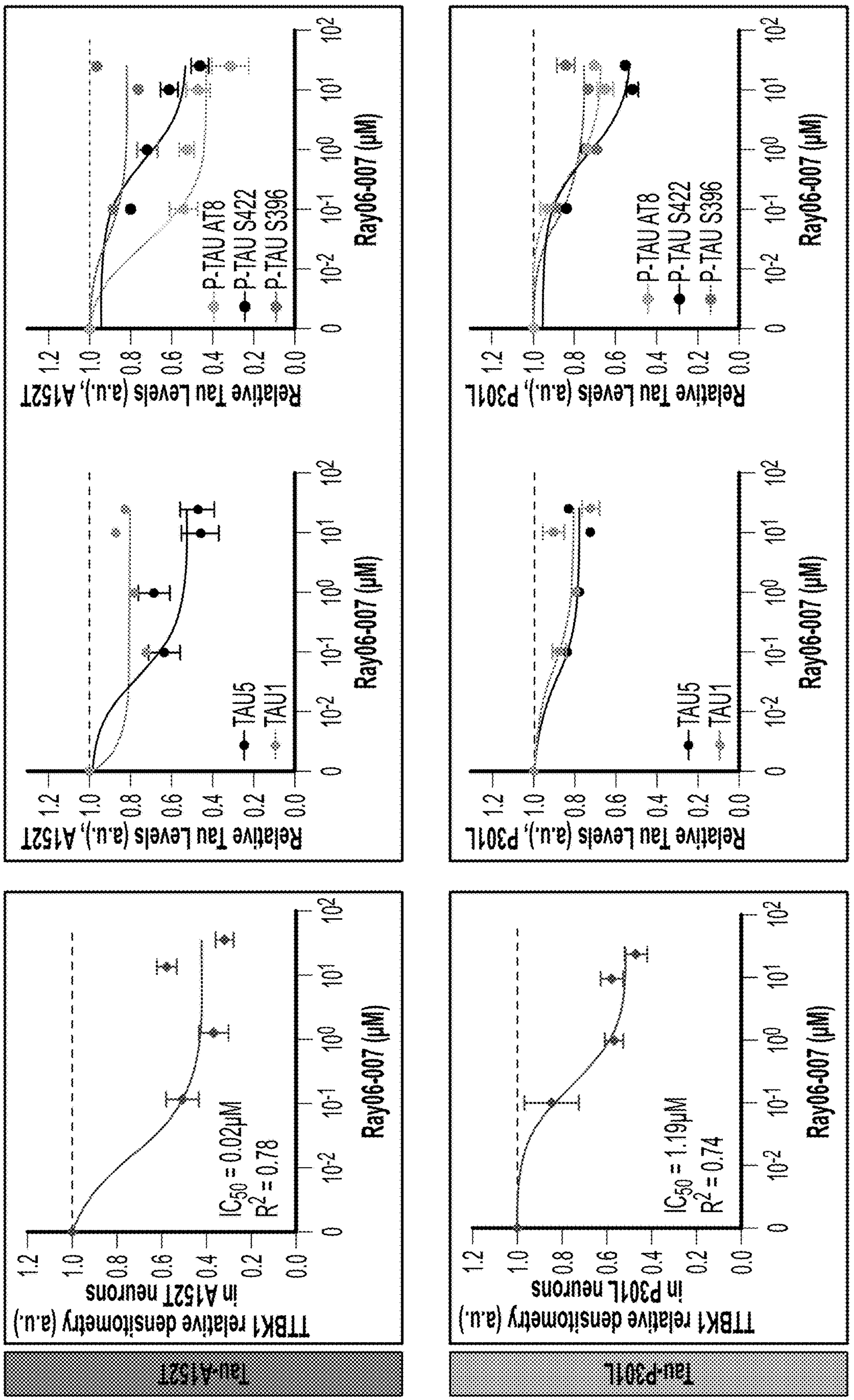

FIG. 12. Illustrates the TTBK1 degrader Ray06-007 showed good dose-dependent effect on TTBK1 protein levels with $IC_{50}$ of 0.02-0.2 μM. Regarding tau, a reduction in total tau was observed mainly in A152T neurons. In this model, reduction in P-tau was more accentuated for the TTBK1-dependent sited AT8 and S422. The % reduction in P-tau and total tau seem to be very similar, possibly due to changes in tau oligomerization and degradation propensity as a consequence of reduced tau phosphorylation. In P301L neurons, the effects in tau and P-tau are less accentuated and mostly observed at higher TTBK imide concentrations.

DETAILED DESCRIPTION

TTBK1 has been linked to tau pathology and thus to Alzheimer's disease and related tauopathies. Published studies demonstrate that TTBK1 levels are increased in Alzheimer's disease post-mortem brain and that TTBK1 phosphorylates tau. TTBK1 has been linked to other neurodegenerative disease, such as amyotrophic lateral sclerosis through phosphorylation of TDP-43. Finally, TTBK1 has also been shown to be involved in neuroinflammation. Taken together, developing selective inhibitors of TTBK1 are expected to have broad utility for the treatment of multiple human diseases of the nervous system. However, due to the observation in the literature that the $K_m$, ATP for TTBK1 is ~10 μM, which is in the low end of 'normal' range for kinases, it has been problematic for the field to develop pharmacologically acceptable, high potency ATP competitive inhibitors since the cellular concentrations of ATP range as high as the millimolar range. The present disclosure provides a set of compounds that are heterobifunctional TTBK1 degraders (e.g., the compounds can target TTBK1 for degradation).

Compounds

In some embodiments, the present disclosure provides a compound of Formula (I):

(I)

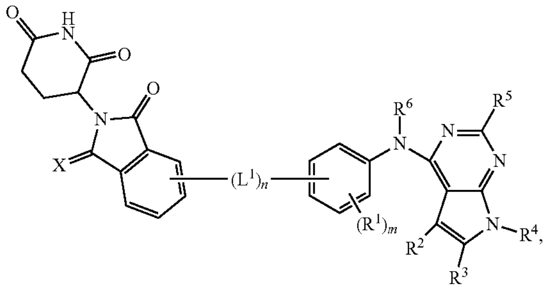

or a pharmaceutically acceptable salt thereof, wherein:

n is an integer selected from 1 to 10;

each $L^1$ is independently selected from C(=O), $N(R^N)$, S, S(=O), $S(=O)_2$, O, $(-C_{1-3}$ alkylene-O$-)_x$, $(-O-C_{1-3}$ alkylene-$)_x$, $-C_{1-10}$ alkylene-, $C_{2-6}$ alkenylene, $C_{2-6}$ alkynylene, $C_{3-10}$ cycloalkylene, $C_{6-10}$ arylene, 5-14 membered heteroarylene, and 4-10 membered heterocycloalkylene, wherein each x is independently an integer from 1 to 10 and each $C_{1-10}$ alkylene, $C_{2-6}$ alkenylene, $C_{2-6}$ alkynylene, $C_{3-10}$ cycloalkylene, $C_{6-10}$ arylene, 5-14 membered heteroarylene, and 4-10 membered heterocycloalkylene is optionally substituted with 1, 2, or 3 substituents independently selected from OH, $NO_2$, CN, halo, amino, and carboxy;

each $R^N$ is independently selected from H, $C_{1-3}$ alkyl, and $C_{1-3}$ haloalkyl;

X is O, or X is absent;

m is an integer from 0 to 4;

each $R^1$ is independently selected from halo, $C_{1-3}$ alkyl, $C_{1-3}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl;

each $R^2$, $R^3$, and $R^5$ is independently selected from H, halo, $C_{1-3}$ alkyl, $C_{1-4}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl; and $R^4$ and $R^6$ are independently selected from H, $C_{1-3}$ alkyl, and $C_{1-3}$ haloalkyl.

In some embodiments:

n is an integer selected from 1 to 10;

each $L^1$ is independently selected from C(=O), N($R^N$), S, S(=O), S(=O)$_2$, O, —$C_{1-3}$ alkylene-O—, —O—$C_{1-3}$ alkylene-, —$C_{1-10}$ alkylene-, $C_{2-6}$ alkenylene, $C_{2-6}$ alkynylene, $C_{3-10}$ cycloalkylene, $C_{6-10}$ arylene, 5-14 membered heteroarylene, and 4-10 membered heterocycloalkylene, wherein each $C_{1-10}$ alkylene, $C_{2-6}$ alkenylene, $C_{2-6}$ alkynylene, $C_{3-10}$ cycloalkylene, $C_{6-10}$ arylene, 5-14 membered heteroarylene, and 4-10 membered heterocycloalkylene is optionally substituted with 1, 2, or 3 substituents independently selected from OH, $NO_2$, CN, halo, amino, and carboxy;

each $R^N$ is independently selected from H, $C_{1-3}$ alkyl, and $C_{1-3}$ haloalkyl;

X is O, or X is absent;

m is an integer from 0 to 4;

each $R^1$ is independently selected from halo, $C_{1-3}$ alkyl, $C_{1-3}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl;

each $R^2$, $R^3$, and $R^5$ is independently selected from H, halo, $C_{1-3}$ alkyl, $C_{1-4}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl; and $R^4$ and $R^6$ are independently selected from H, $C_{1-3}$ alkyl, and $C_{1-3}$ haloalkyl.

In some embodiments:

n is an integer selected from 1 to 10;

each $L^1$ is independently selected from C(=O), N($R^N$), S, S(=O), S(=O)$_2$, O, —$C_{1-3}$ alkylene-O—, —O—$C_{1-3}$ alkylene-, —$C_{1-10}$ alkylene-, $C_{2-6}$ alkenylene, and $C_{2-6}$ alkynylene;

each $R^N$ is independently selected from H, $C_{1-3}$ alkyl, and $C_{1-3}$ haloalkyl;

X is O, or X is absent;

m is an integer from 0 to 4;

each $R^1$ is independently selected from halo, $C_{1-3}$ alkyl, $C_{1-3}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl;

each $R^2$, $R^3$, and $R^5$ is independently selected from H, halo, $C_{1-3}$ alkyl, $C_{1-4}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl; and $R^4$ and $R^6$ are independently selected from H, $C_{1-3}$ alkyl, and $C_{1-3}$ haloalkyl.

In some embodiments:

n is an integer selected from 1 to 10;

each $L^1$ is independently selected from C(=O), N($R^N$), S, S(=O), S(=O)$_2$, O, —$C_{1-3}$ alkylene-O—, —O—$C_{1-3}$ alkylene-, —$C_{1-10}$ alkylene-, $C_{2-6}$ alkenylene, and $C_{2-6}$ alkynylene;

each $R^N$ is independently selected from H, $C_{1-3}$ alkyl, and $C_{1-3}$ haloalkyl;

X is O, or X is absent;

m is an integer from 0 to 4;

each $R^1$ is independently selected from halo, $C_{1-3}$ alkyl, $C_{1-3}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl;

each $R^2$, $R^3$, and $R^5$ is independently selected from H, halo, $C_{1-3}$ alkyl, $C_{1-4}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl; and $R^4$ and $R^6$ are independently selected from H, $C_{1-3}$ alkyl, and $C_{1-3}$ haloalkyl.

In some embodiments:

n is an integer selected from 3 to 6;

each $L^1$ is independently selected from C(=O), N($R^N$), S, S(=O), S(=O)$_2$, O, —$C_{1-3}$ alkylene-O—, —O—$C_{1-3}$ alkylene-, —$C_{1-10}$ alkylene-, $C_{2-6}$ alkenylene, and $C_{2-6}$ alkynylene;

each $R^N$ is independently selected from H, $C_{1-3}$ alkyl, and $C_{1-3}$ haloalkyl;

X is O, or X is absent;

m is an integer from 0 to 4;

each $R^1$ is independently selected from halo, $C_{1-3}$ alkyl, $C_{1-3}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl;

each $R^2$, $R^3$, and $R^5$ is independently selected from H, halo, $C_{1-3}$ alkyl, $C_{1-4}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl; and $R^4$ and $R^6$ are independently selected from H, $C_{1-3}$ alkyl, and $C_{1-3}$ haloalkyl.

In some embodiments, wherein X is O.

In some embodiments, wherein X is absent. When X is absent, the carbon atom of C=X becomes $CH_2$.

In some embodiments, x is 1 or 2. In some embodiments, x is 1. In some embodiments, x is 2. In some embodiments, x is 3 to 6. In some embodiments, x is 7 to 10.

In some embodiments, the compound of Formula (I) has formula:

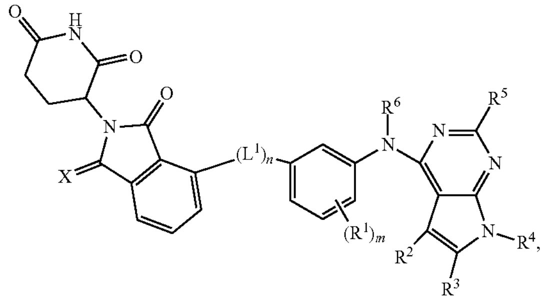

or a pharmaceutically acceptable salt thereof.

In some embodiments, the compound of Formula (I) has formula:

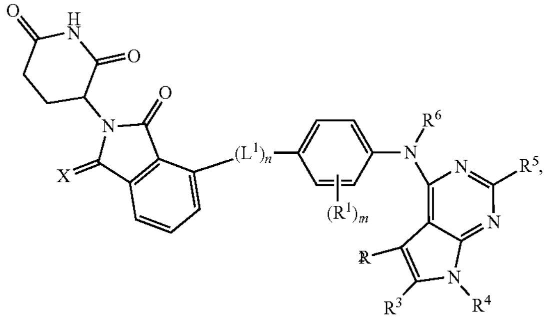

or a pharmaceutically acceptable salt thereof.

In some embodiments, the compound of Formula (I) has formula:

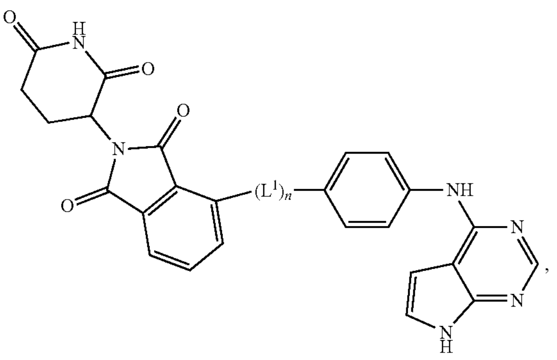

or a pharmaceutically acceptable salt thereof.

In some embodiments, the compound of Formula (I) has formula:

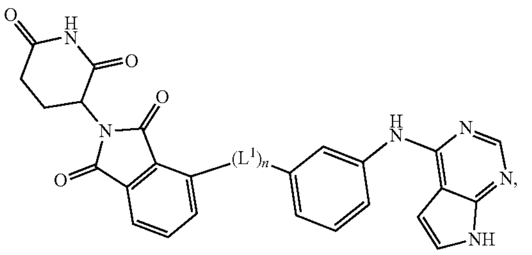

or a pharmaceutically acceptable salt thereof.

In some embodiments, n is an integer from 1 to 8. In some embodiments, n is an integer from 2 to 6. In some embodiments, n is an integer from 3 to 5. In some embodiments, n is an integer from 3 to 8.

In some embodiments, n is 3. In some embodiments, n is 4. In some embodiments, n is 5. In some embodiments, n is 6.

In some embodiments, each $L^1$ is independently selected from C(═O), NH, O, and —$C_{1-10}$ alkylene-.

In some embodiments, each $L^1$ is independently selected from C(═O), O, and —$C_{1-10}$ alkylene-.

In some embodiments, when $L^1$ includes more than one of any of C(═O), N($R^N$), S, S(═O), S(═O)$_2$, O, the two groups are not adjacent in $L^1$. For example, in some embodiments, $L^1$ does not include a —O—O— moiety, or a —N—O— moiety.

In some embodiments, moiety -(L')$_n$- comprises a group selected from O, N($R^N$), S, C(═O), C(═O)O, C(═O)N($R^N$), N($R^N$)C(═O), N($R^N$)C(═O)O, N($R^N$)C(═O)N($R^N$), OC(═O), OC(═O)O, OC(═O)N($R^N$), S(O)$_2$N($R^N$), and N($R^N$)S(O)$_2$, or a combination thereof.

In some embodiments, moiety -(L')$_n$- can be selected from any of the L groups recited in U.S. patent application Ser. No. 14/792,414, or U.S. patent application Ser. No. 14/707,930, which are incorporated herein by reference in their entirety.

In some embodiments, the compound of Formula (I) has formula:

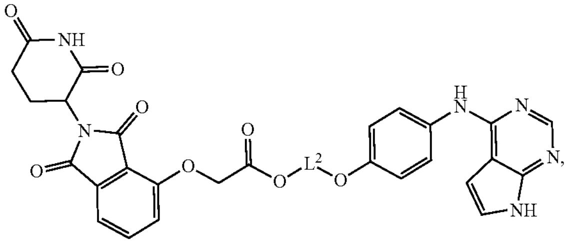

or a pharmaceutically acceptable salt thereof, wherein:

$L^2$ is —$C_{1-10}$ alkylene-.

In some embodiments, the compound of Formula (I) has formula:

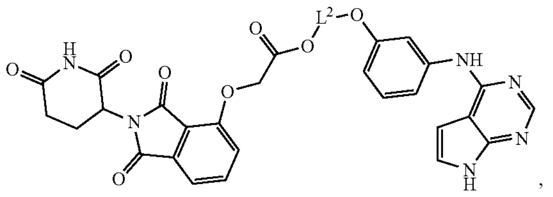

or a pharmaceutically acceptable salt thereof, wherein:

$L^2$ is —$C_{1-10}$ alkylene-.

In some embodiments, $L^2$ is butylene.

In some embodiments, $L^2$ is hexylene.

In some embodiments, $L^2$ is octylene.

In some embodiments, the compound of Formula (I) is selected from any one of the following compounds:

(Ray06-002)
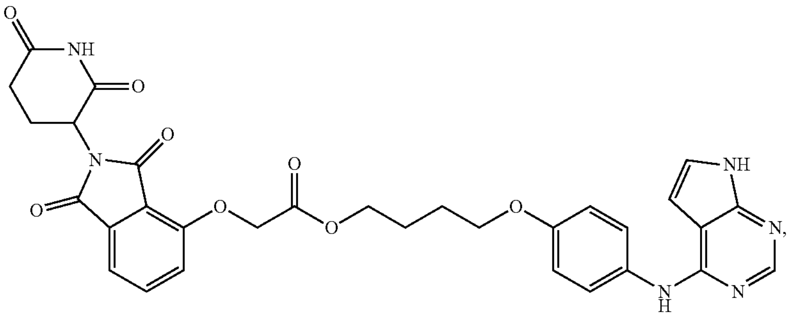
(Ray06-003)
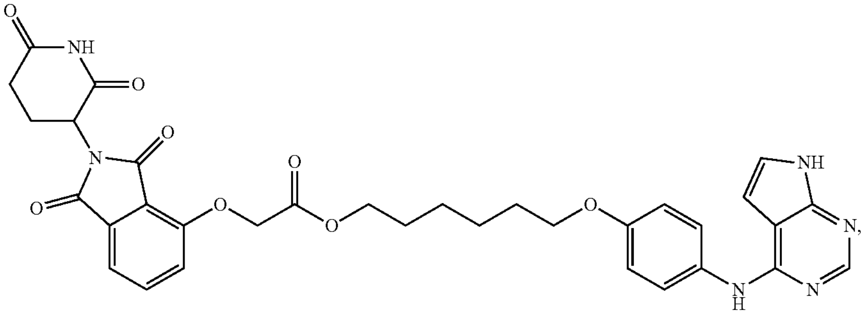
(Ray06-004)
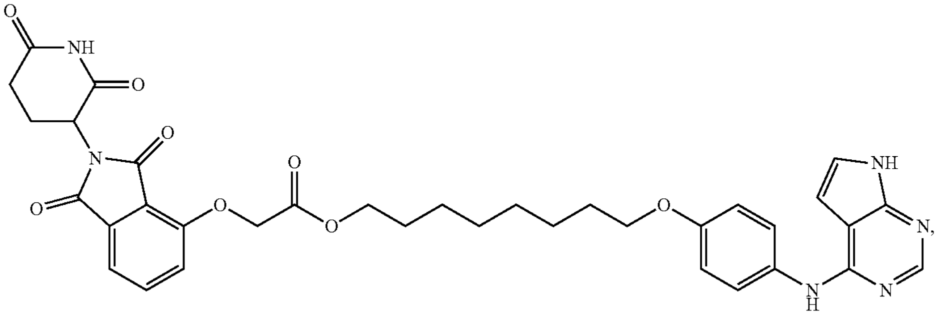
(Ray06-005)
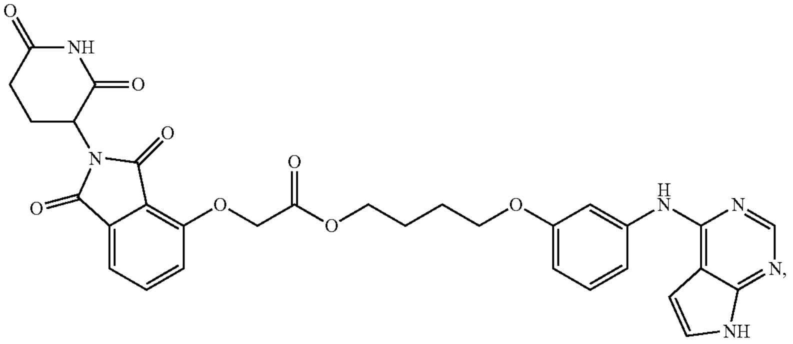

-continued
(Ray06-006)
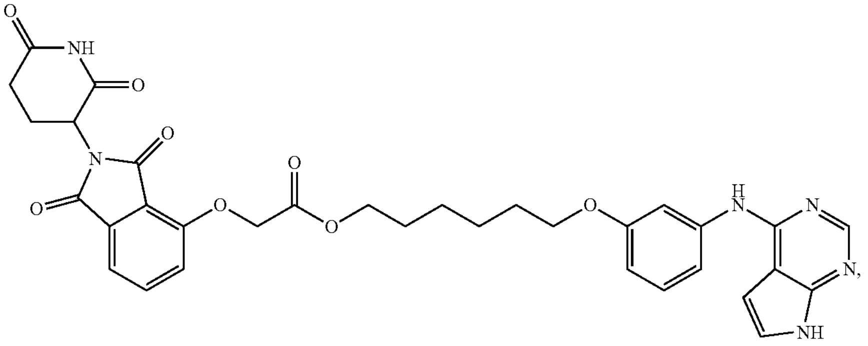
and
(Ray06-007)
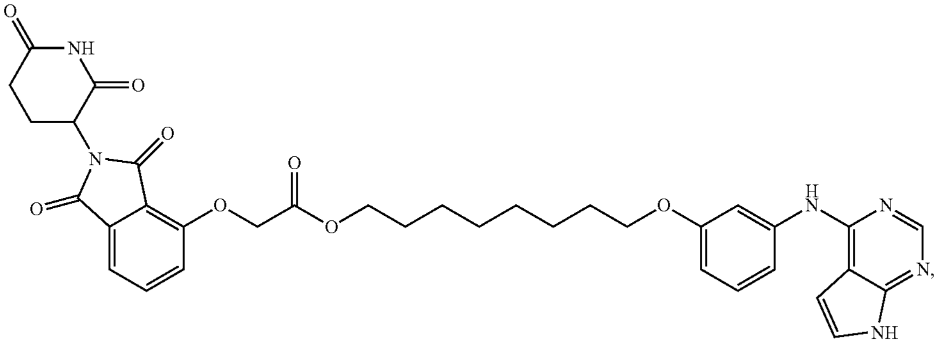
or a pharmaceutically acceptable salt thereof.
In some embodiments, the compound of Formula (I) is
(Ray06-002)
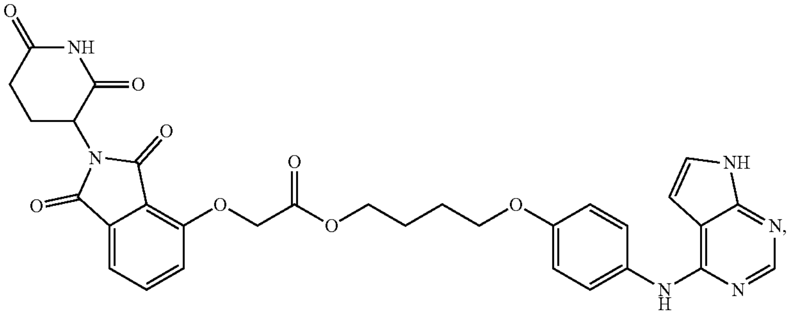
or a pharmaceutically acceptable salt thereof.

In some embodiments, the compound of Formula (I) is
(Ray06-003)
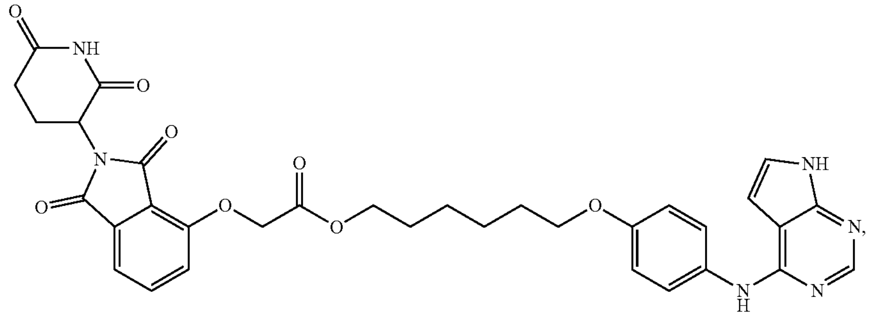
or a pharmaceutically acceptable salt thereof.
In some embodiments, the compound of Formula (I) is
(Ray06-004)
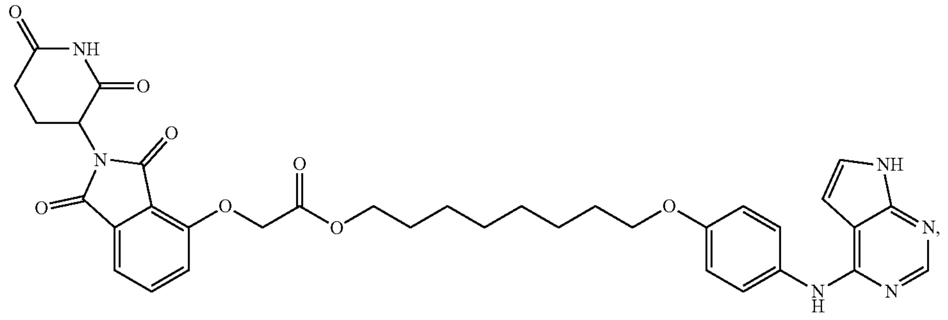
or a pharmaceutically acceptable salt thereof.
In some embodiments, the compound of Formula (I) is
(Ray06-005)
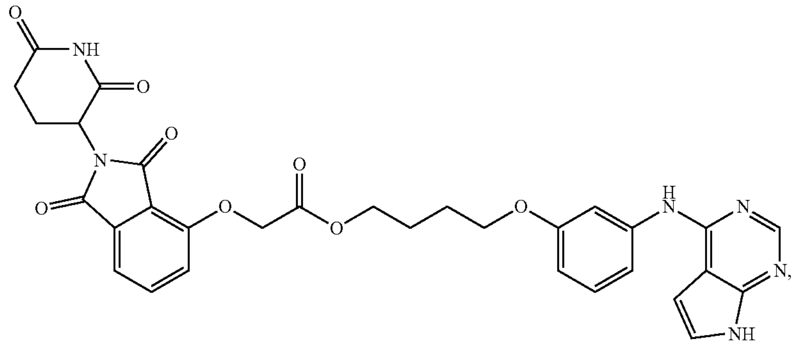
or a pharmaceutically acceptable salt thereof.

In some embodiments, the compound of Formula (I) is (Ray06-006)

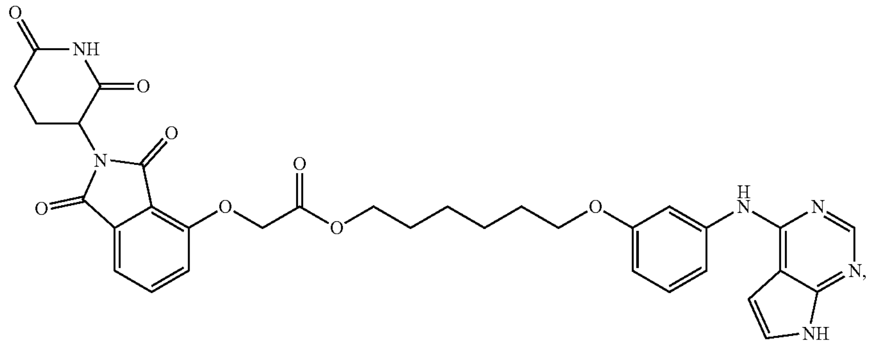

or a pharmaceutically acceptable salt thereof.

In some embodiments, the compound of Formula (I) is (Ray06-007)

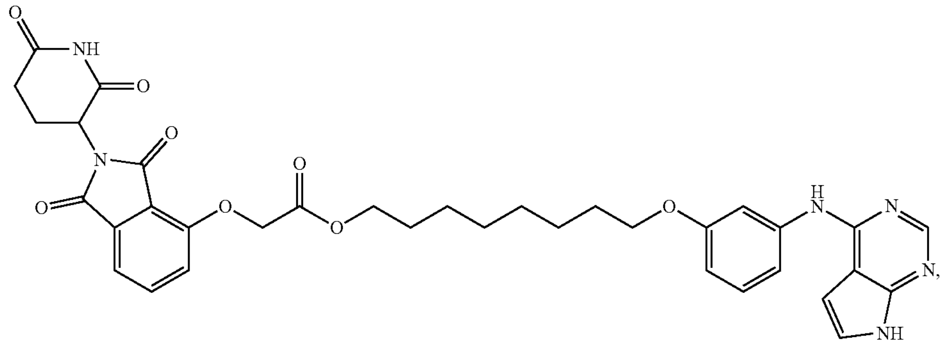

or a pharmaceutically acceptable salt thereof.

Pharmaceutically Acceptable Salts

In some embodiments, a salt of a compound of Formula (I) is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formula (I) include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formula (I) include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—($C_1$-$C_6$)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like. In some embodiments, the compounds of Formula (I), or pharmaceutically acceptable salts thereof, are substantially isolated.

Methods of Use

In some embodiments, the present disclosure provides a method of inhibiting Tau-Tubulin Kinase-1 (TTBK1), the method comprising contacting the TTBK1 with an effective amount of a compound of Formula (I), or a pharmaceutically acceptable salt thereof.

In some embodiments, the present disclosure provides a method of inhibiting Tau-Tubulin Kinase-1 (TTBK1) in a cell, the method comprising contacting the cell with an effective amount of a compound of Formula (I), or a pharmaceutically acceptable salt thereof. In some embodiments, the contacting is carried out in vitro, ex vivo, or in vivo.

In some embodiments, the present disclosure provides a method of inhibiting Tau-Tubulin Kinase-1 (TTBK1) in a subject, the method comprising administering to the subject a therapeutically effective amount of a compound of Formula (I), or a pharmaceutically acceptable salt thereof.

In some embodiments, the present disclosure provides a method of treating a neurodegenerative disease or disorder in a subject in need thereof, comprising administering to the subject a therapeutically effective amount of a compound of Formula (I), or a pharmaceutically acceptable salt thereof, or a pharmaceutical composition comprising same. In some embodiments, the neurodegenerative disease or disorder is selected from tauopathy, Alzheimer's disease, frontotemporal dementia, amyotrophic lateral sclerosis, multiple sclerosis, frontotemporal lobar degeneration with tau pathology, Huntington's disease, and Parkinson's disease, the method comprising administering to the subject in need thereof a therapeutically effective amount of a compound of Formula (I), or a pharmaceutically acceptable salt thereof, or a pharmaceutical composition comprising same.

In some embodiments, the present disclosure provides a method of treating a neurodegenerative disease or disorder in a subject in need thereof, comprising administering to the subject in need thereof a therapeutically effective amount of a compound of Formula (I), or a pharmaceutically acceptable salt thereof, or a pharmaceutical composition comprising same, wherein the neurodegenerative disease or disorder is selected from tauopathy, Alzheimer's disease, frontotemporal dementia, amyotrophic lateral sclerosis, multiple sclerosis, frontotemporal lobar degeneration with tau pathology, Huntington's disease, and Parkinson's disease.

In some embodiments, the neurodegenerative disease or disorder is Alzheimer's disease. In some embodiments, the neurodegenerative disease or disorder is tauopathy. In some embodiments, the neurodegenerative disease or disorder is frontotemporal dementia. In some embodiments, the neurodegenerative disease or disorder is amyotrophic lateral sclerosis. In some embodiments, the neurodegenerative disease or disorder is progressive supranuclear palsy.

In some embodiments, the tauopathy is selected from Primary age-related tauopathy (PART), Chronic traumatic encephalopathy (CTE), Progressive supranuclear palsy (PSP), Corticobasal degeneration (CBD), Frontotemporal dementia and parkinsonism linked to chromosome 17 (FTDP-17), Lytico-bodig disease (Parkinson-dementia complex of Guam), Ganglioglioma and gangliocytoma, Meningioangiomatosis, Postencephalitic parkinsonism, Subacute sclerosing panencephalitis (SSPE), Argyrophilic grain disease (AGD), lead encephalopathy, tuberous sclerosis, pantothenate kinase-associated neurodegeneration, lipofuscinosis, and Pick's disease. In some embodiments, the tauopathy is progressive supranuclear palsy. In some embodiments, the tauopathy is Primary age-related tauopathy (PART). In some embodiments, the tauopathy is Chronic traumatic encephalopathy (CTE). In some embodiments, the tauopathy is Progressive supranuclear palsy (PSP). In some embodiments, the tauopathy is Corticobasal degeneration (CBD). In some embodiments, the tauopathy is Frontotemporal dementia and parkinsonism linked to chromosome 17 (FTDP-17). In some embodiments, the tauopathy is Lytico-bodig disease (Parkinson-dementia complex of Guam). In some embodiments, the tauopathy is Ganglioglioma and gangliocytoma, In some embodiments, the tauopathy is Meningioangiomatosis. In some embodiments, the tauopathy is Postencephalitic parkinsonism. In some embodiments, the tauopathy is Subacute sclerosing panencephalitis (SSPE). In some embodiments, the tauopathy is Argyrophilic grain disease (AGD). In some embodiments, the tauopathy is lead encephalopathy. In some embodiments, the tauopathy is tuberous sclerosis. In some embodiments, the tauopathy is pantothenate kinase-associated neurodegeneration. In some embodiments, the tauopathy is lipofuscinosis. In some embodiments, the tauopathy is Pick's disease.

Pharmaceutical Compositions

The present application also provides pharmaceutical compositions comprising an effective amount of a compound of the present disclosure (e.g., Formula (I)) disclosed herein, or a pharmaceutically acceptable salt thereof, and a pharmaceutically acceptable carrier. The pharmaceutical composition may also comprise any one of the additional therapeutic agents described herein. In certain embodiments, the application also provides pharmaceutical compositions and dosage forms comprising any one of the additional therapeutic agents described herein. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants, and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

The compositions or dosage forms may contain any one of the compounds and therapeutic agents described herein in the range of 0.005% to 100% with the balance made up of suitable pharmaceutically acceptable excipients. The contemplated compositions may contain 0.001%-100% of any one of the compounds and therapeutic agents provided herein, in one embodiment 0.1-95%, in another embodiment 75-85%, in a further embodiment 20-80%, wherein the balance may be made up of any pharmaceutically acceptable excipient described herein, or any combination of these excipients.

Routes of Administration and Dosage Forms

The pharmaceutical compositions of the present application include those suitable for any acceptable route of administration. Acceptable routes of administration include, but are not limited to, buccal, cutaneous, endocervical, endosinusial, endotracheal, enteral, epidural, interstitial, intra-abdominal, intra-arterial, intrabronchial, intrabursal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intranasal, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal.

Compositions and formulations described herein may conveniently be presented in a unit dosage form, e.g., tablets, sustained-release capsules, and in liposomes, and may be prepared by any methods well known in the art of pharmacy. See, for example, Remington: The Science and Practice of Pharmacy, Lippincott Williams & Wilkins, Baltimore, MD (20th ed. 2000). Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, any one of the compounds and therapeutic agents disclosed herein are administered orally. Compositions of the present application suitable for oral administration may be presented as discrete units such as capsules, sachets, granules or tablets each containing a predetermined amount (e.g., effective amount) of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In the case of tablets for oral use, carriers that are commonly used include lactose, sucrose, glucose, mannitol, and silicic acid and starches. Other acceptable excipients may include: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added. Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions or infusion solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, saline (e.g., 0.9% saline solution) or 5% dextrose solution, immediately prior to use. Extemporaneous injection solutions and suspensions may be prepared from sterile powders, granules and tablets. The injection solutions may be in the form, for example, of a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031. Additional formulations and methods for intranasal administration are found in Ilium, L., *J Pharm Pharmacol,* 56:3-17, 2004 and Ilium, L., *Eur J Pharm Sci* 11:1-18, 2000.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form. Topical administration of the pharmaceutical compositions of the present application is especially useful when the desired treatment involves areas or organs readily accessible by topical application. In some embodiments, the topical composition comprises a combination of any one of the compounds and therapeutic agents disclosed herein, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

The compounds and therapeutic agents of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides an implantable drug release device impregnated with or containing a compound or a therapeutic agent, or a composition comprising a compound of the present application or a therapeutic agent, such that said compound or therapeutic agent is released from said device and is therapeutically active.

Dosages and Regimens

In the pharmaceutical compositions of the present application, a compound of the present disclosure (e.g., a compound of Formula (I)) is present in an effective amount (e.g., a therapeutically effective amount). Effective doses may vary, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, an effective amount of the compound of Formula (I) can range, for example, from about 0.001 mg/kg to about 500 mg/kg (e.g., from about 0.001 mg/kg to about 200 mg/kg; from about 0.01 mg/kg to about 200 mg/kg; from about 0.01 mg/kg to about 150 mg/kg; from about 0.01 mg/kg to about 100 mg/kg; from about 0.01 mg/kg to about 50 mg/kg; from about 0.01 mg/kg to about 10 mg/kg; from about 0.01 mg/kg to about 5 mg/kg; from about 0.01 mg/kg to about 1 mg/kg; from about 0.01 mg/kg to about 0.5 mg/kg; from about 0.01 mg/kg to about 0.1 mg/kg; from about 0.1 mg/kg to about 200 mg/kg; from about 0.1 mg/kg to about 150 mg/kg; from about 0.1 mg/kg to about 100 mg/kg; from about 0.1 mg/kg to about 50 mg/kg; from about 0.1 mg/kg to about 10 mg/kg; from about 0.1 mg/kg to about 5 mg/kg; from about 0.1 mg/kg to about 2 mg/kg; from about 0.1 mg/kg to about 1 mg/kg; or from about 0.1 mg/kg to about 0.5 mg/kg). In some embodiments, an effective amount of a compound of Formula (I) is about 0.1 mg/kg, about 0.5 mg/kg, about 1 mg/kg, about 2 mg/kg, or about 5 mg/kg.

The foregoing dosages can be administered on a daily basis (e.g., as a single dose or as two or more divided doses, e.g., once daily, twice daily, thrice daily) or non-daily basis (e.g., every other day, every two days, every three days, once weekly, twice weekly, once every two weeks, once a month).

Kits

The present invention also includes pharmaceutical kits useful, for example, in the treatment of disorders, diseases and conditions referred to herein, which include one or more containers containing a pharmaceutical composition comprising a therapeutically effective amount of a compound of the present disclosure. Such kits can further include, if desired, one or more of various conventional pharmaceutical kit components, such as, for example, containers with one or more pharmaceutically acceptable carriers, additional containers, etc. Instructions, either as inserts or as labels, indicating quantities of the components to be administered, guidelines for administration, and/or guidelines for mixing the components, can also be included in the kit. The kit may optionally include an additional therapeutic agent as described herein.

Definitions

As used herein, the term "about" means plus or minus approximately 10% of the indicated value.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, "$C_{n-m}$haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "amino" refers to a group of formula —$NH_2$.

As used herein, the term "$C_{n-m}$alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "di($C_{n-m}$-alkyl)amino" refers to a group of formula —$N(alkyl)_2$, wherein the two alkyl groups each has, independently, n to m carbon atoms. In some embodiments, each alkyl group independently has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "carboxy" refers to a —C(O)OH group.

As used herein, "halo" refers to F, Cl, Br, or I. In some embodiments, a halo is F, Cl, or Br.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to 10 carbon atoms. In some embodiments, the aryl group is phenyl or naphtyl. In some embodiments, the term "arylene" refers to a divalent aryl group.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by 1 or 2 independently selected oxo or sulfide groups (e.g., C(O) or C(S)). Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, or 10 ring-forming carbons ($C_{3-10}$). In some embodiments, the cycloalkyl is a $C_{3-10}$ monocyclic or bicyclic cyclocalkyl. In some embodiments, the cycloalkyl is a $C_{3-7}$ monocyclic cyclocalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. In some embodiments, cycloalkyl is cyclopropyl, cyclobutyl, cyclopentyl, or cyclohexyl. In some embodiments, the term "cycloalkylene" refers to a divalent cycloalkyl group.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl is a 5-10 membered monocyclic or bicyclic heteroaryl having 1, 2, 3 or 4 heteroatom ring members independently selected from nitrogen, sulfur and oxygen. In some embodiments, the heteroaryl is a 5-6 monocyclic heteroaryl having 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl. In some embodiments, the term "heteroarylene" refers to a divalent heteroaryl group.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by 1 or 2 independently selected oxo or sulfido groups (e.g., C(O), S(O), C(S), or $S(O)_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl is a monocyclic 4-6 membered heterocycloalkyl having 1 or 2 heteroatoms independently selected from nitrogen, oxygen, or sulfur and having one or more oxidized ring members. In some embodiments, the heterocycloalkyl is a monocyclic or bicyclic 4-10 membered heterocycloalkyl having 1, 2, 3, or 4 heteroatoms independently selected from nitrogen, oxygen, or sulfur and having one or more oxidized ring members. In some embodiments, the term "heterocycloalkylene" refers to a divalent heterocycloalkyl group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

The term "aromatic" refers to a carbocycle or heterocycle having one or more polyunsaturated rings having aromatic character (i.e., having (4n+2) delocalized 71 (pi) electrons where n is an integer).

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds, N═N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the Tau-Tubulin Kinase-1 (TTBK1) with a compound of the invention includes the administration of a compound of the present invention to an individual or patient, such as a human, having Tau-Tubulin Kinase-1 (TTBK1), as well as, for example, introducing a compound of the invention into a sample containing a cellular or purified preparation containing the Tau-Tubulin Kinase-1 (TTBK1).

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

EXAMPLES

Chemical Synthesis Methods & Analytical Chemistry $^{1}H$ NMR spectra were recorded on a Bruker AV-III-400 or 500 MHz NMR spectrometer. Chemical shifts are reported in δ values in ppm downfield from TMS as the internal standard. $^{1}H$ NMR data are reported as follows: chemical shift, multiplicity (s=singlet, d=doublet, t=triplet, q=quartet, b=broad, m=multiplet, quint=quintate), coupling constant (Hz), integration. $^{13}C$ chemical shifts are reported in S values in ppm downfield from TMS as the internal standard. Low resolution mass spectra were obtained on Waters Acquity Ultra Performance LC with electrospray ionization and SQ detector by injecting sample in a steady flow of 1 mM ammonium acetate in 20% water-acetonitrile at the rate of 0.2 mL/min. The purity of compounds were determined by analytical HPLC, performed on a Shimadzu Prominence-HPLC with ELSD PDA multi, and a Gemini NX C-18 column (250×4.6 mm, 5μ) with mobile phase (A) 0.1% formic acid in acetonitrile and mobile phase (B) 0.1% formic acid in water using following gradient of B/A (0 min, 10%), (5 min, 90%), (6 min, 95%) and (10 min, 95%), at 1.0 mL/min flow rate. Analytical thin layer chromatography was performed on 250 μM silica gel $F_{254}$ plates. Preparative thin layer chromatography was performed on 1000 μM silica gel $F_{254}$ plates. Flash column chromatography was performed employing 230-400 mesh silica gel.

Example 1: Methyl 2-bromo-5-(7H-pyrrolo[2,3-d]pyrimidin-4-ylamino)benzoate (Ray06-01)

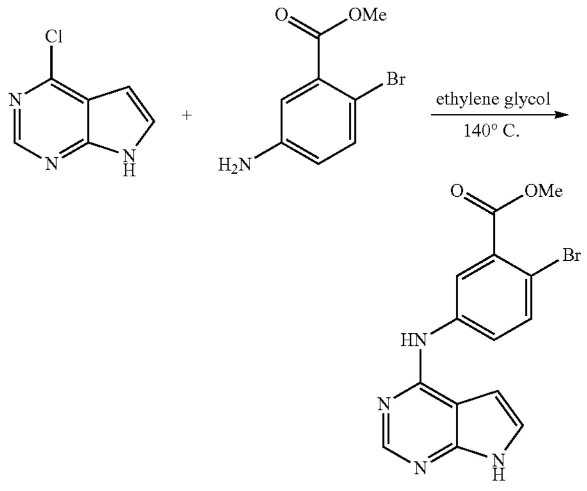

Ray06-001

A solution of 6-chloro-7-deazapurine (78 mg, 0.49 mmol) and methyl 5-amino-2-bromobenzoate (120 mg, 0.52 mmol) in ethylene glycol was heated at 140° C. and stirred for 3 h. The reaction mixture was diluted with EtOAc (40 mL) and washed with water (3×10 mL). The organic layer was dried over $Na_2SO_4$, concentrated, and recrystallized from $CH_2Cl_2$ to obtain title compound (90 mg) as a brown solid. $^1H$ NMR (400 MHz, DMSO-$d_6$) δ 11.85 (bs, 1H), 9.61 (s, 1H), 8.36-8.32 (m, 2H), 8.21 (dd, J=2.8, 8.8 Hz, 1H), 7.70 (d, J=8.8 Hz, 1H), 7.29 (dd, J=2.4, 3.2 Hz, 1H), 6.82 (dd, J=1.6, 3.2 Hz, 1H), 3.89 (s, 3H). HPLC: $t_R$=6.12 min, 97.4%.

Example 2

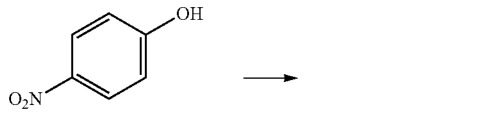

4-nitrophenol

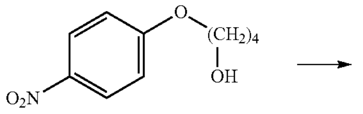

2a

-continued

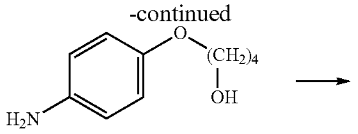

3a

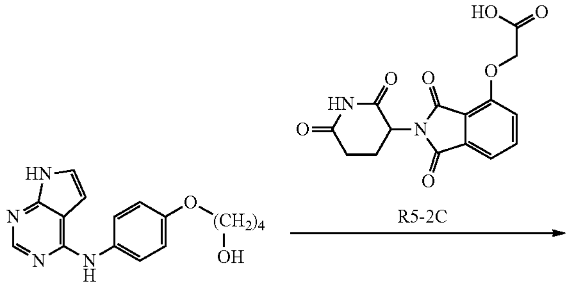

4a

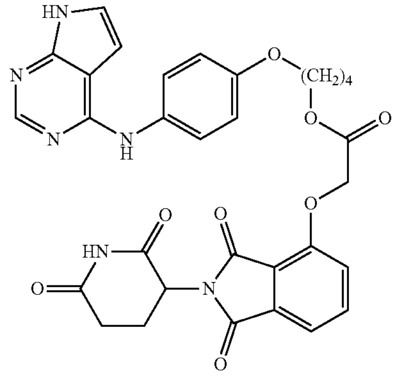

Ray06-002

Step 1

To a solution of 4-O-TBS-butyl-1-tosylate (1.30 mg, 4.6 mmol) and 4-nitrophenol (600 mg, 4.3 mmol) in dry dimethylformamide (DMF) (25 mL) was added $K_2CO_3$ (1.27 g, 9.2 mmol) and heated at 70° C. for 4 hours. The reaction mixture was concentrated, diluted with water (2 mL) and brine (8 mL) and extracted with $CHCl_3$ (3×30 mL). The organic layer was dried over $Na_2SO_4$, filtered, and concentrated. The crude material was dissolved in dry tetrahydrofuran (THF) (10 mL), cooled, and treated with 1M tetra-n-butylammonium fluoride (TBAF) in THE (5 ml, 5 mmol). The resulting mixture was stirred for 2 hours. The reaction mixture was concentrated, diluted with ethyl acetate (50 mL), and washed with water (2×10 mL) and brine (10 mL). The organic layer was dried over $Na_2SO_4$, filtered, concentrated, and purified by silica gel column chromatography to obtain Compound 2a.

4-(4-Nitrophenoxy)-1-butanol (Compound 2a). $^1H$ NMR (400 MHz, $CDCl_3$) δ 8.23-8.17 (m, 2H), 6.97-6.92 (m, 2H), 4.10 (t, J=6.4 Hz, 2H), 3.78-3.71 (m, 2H), 1.99-1.89 (m, 2H), 1.82-1.72 (m, 2H), 1.43-1.36 (m, 1H).

Step 2

To a solution of Compound 2a (1 eqv) in 80% EtOH-water (5 mL) was add iron powder (6 eqv) and $CaCl_2$) (0.6 eqv). The reaction mixture was refluxed for 2 hours. The reaction mixture was cooled to ambient temperature and concentrated. The crude product was then diluted with water (5 mL) and extracted with ethyl acetate (2×10 mL). The organic layer was dried over $Na_2SO_4$, concentrated and purified by silica gel column chromatography to obtain Compound 3a.

4-(4-Aminophenoxy)-1-butanol (Compound 3a). $^1$H NMR (400 MHz, $CDCl_3$) δ 6.77-6.71 (m, 2H), 6.67-6.62 (m, 2H), 3.93 (t, J=6.0 Hz, 2H), 3.71 (t, J=6.0 Hz, 2H), 3.42 (bs, 2H), 1.88-1.81 (m, 2H), 1.79-1.70 (m, 2H).

Step 3

A solution of 6-chloro-7-deazapurine (1 eqv) and Compound 3a (1 eqv) in ethylene glycol (2 mL) was heated at 120° C. and stirred for 3 hours. The reaction mixture was diluted with brine (20 mL) and extracted with 10% MeOH—$CHCl_3$ (10×25 mL). The organic layer was dried over $Na_2SO_4$, concentrated, and purified by silica gel column chromatography (MeOH—$CHCl_3$) to obtain Compound 4a.

4-(4-[(7H-pyrrolo[2,3-d]pyrimidin-4-yl)amino]phenoxy)-1-butanol (Compound 4a) MS (ESI$^+$) m/z 327.4 (M+H)$^+$. $^1$H NMR (500 MHz, DMSO-$d_6$) δ □12.59 (bs, 1H), 10.83 (bs, 1H), 8.26 (s, 1H), 7.49 (d, J=9.0 Hz, 2H), 7.39 (s, 1H), 7.06 (d, J=9.0 Hz, 2H), 6.76 (bs, 1H), 4.02 (t, J=6.5 Hz, 2H), 3.46 (t, J=6.5 Hz, 2H), 1.81-1.73 (m, 2H), 1.62-1.55 (m, 2H).

Step 4

To a solution of Compound 4a (55 mg, 0.11 mmol), R5-2C (45 mg, 0.105 mmol) and HOBt (30 mg, 0.2 mmol) in dry DMF (1 mL) was added triethylamine (20 mg, 0.2 mmol) and N-Ethyl-N'-(3-dimethylaminopropyl)carbodiimide hydrochloride (EDC-HCl) (40 mg, 0.2 mmol). The reaction mixture was stirred at room temperature for 18 hours. The reaction mixture was concentrated under vacuum, diluted with water (5 mL) and extracted with ethyl acetate (2×10 mL). The organic layer was dried over $Na_2SO_4$, concentrated and purified by preparative TLC (8% EtOH in $CHCl_3$) to obtain Ray06-002.

4-(4-(7H-pyrrolo[2,3-d]pyrimidin-4-ylamino)phenoxy)butyl-2-(2-(2,6-dioxopiperidin-3-yl)-1,3-dioxoisoindolin-4-yloxy)acetate (Ray06-002). $^1$H NMR (400 MHz, DMSO-$d_6$) δ 11.69 (bs, 1H), 11.11 (s, 1H), 9.17 (bs, 1H), 8.19 (s, 1H), 7.82-7.76 (m, 1H), 7.70 (d, J=8.8 Hz, 2H), 7.51-7.40 (m, 2H), 7.20-7.16 (m, 1H), 6.92 (d, J=8.8 Hz, 2H), 6.67 (bs, 1H), 5.14-5.07 (m, 3H), 4.21 (t, J=5.6 Hz, 2H), 3.66 (t, J=5.6 Hz, 2H), 2.95-2.83 (m, 1H), 2.71-2.57 (m, 2H), 2.08-1.99 (m, 1H), 1.80-1.73 (m, 4H). HPLC: $t_R$=5.49 min, 98.7%.

Example 3

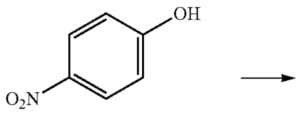

4-nitrophenol

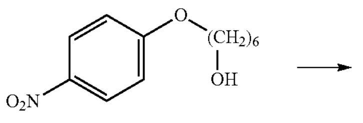

2b

-continued

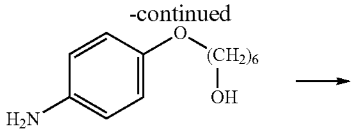

3b

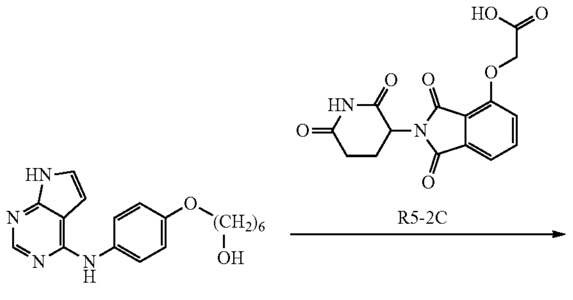

4b

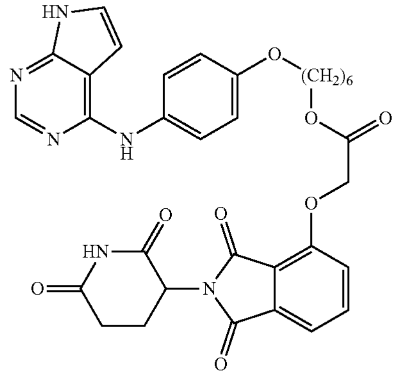

Ray06-003

Step 1

To a solution of 4-nitrophenol (1 eqv) and 6-bromo-1-hexanol (1 eqv) in dry DMF (2.5 ml) was added $K_2CO_3$ (2 eqv). The reaction mixture was stir at 80° C. for 2 hours. The reaction mixture was concentrated, diluted with water (2 mL) and brine (8 mL), and extracted with $CHCl_3$ (3×30 mL). The organic layer was dried over $Na_2SO_4$, filtered, concentrated, and purified by silica gel column chromatography to obtain Compound 2b. 6-(4-Nitrophenoxy)-1-hexanol (Compound 2b). $^1$H NMR (400 MHz, $CDCl_3$) δ □8.20 (m, 2H), 6.94 (m, 2H), 4.05 (t, J=6.4 Hz, 2H), 3.67 (t, J=6.4 Hz, 2H), 1.89-1.81 (m, 2H), 1.67-1.59 (m, 2H), 1.56-1.41 (m, 4H).

Step 2

To a solution of Compound 2b (1 eqv) in 80% EtOH-water (5 mL) was add iron powder (6 eqv) and $CaCl_2$) (0.6 eqv). The reaction mixture was refluxed for 2 hours. The reaction mixture was cooled to ambient temperature and concentrated. The crude product was then diluted with water (5 mL) and extracted with ethyl acetate (2×10 mL). The organic layer was dried over $Na_2SO_4$, concentrated and purified by silica gel column chromatography to obtain Compound 3b.

6-(4-Aminophenoxy)-1-hexanol (Compound 3b). $^1$H NMR (400 MHz, $CDCl_3$) δ□6.76-6.71 (m, 2H), 6.66-6.61 (m, 2H), 3.88 (t, J=6.4 Hz, 2H), 3.65 (t, J=6.4 Hz, 2H), 1.80-1.71 (m, 2H), 1.64-1.54 (m, 2H), 1.52-1.41 (m, 4H).

Step 3

A solution of 6-chloro-7-deazapurine (1 eqv) and Compound 3b (1 eqv) in ethylene glycol (2 mL) was heated at 120° C. and stirred for 3 hours. The reaction mixture was diluted with brine (20 mL) and extracted with 10% MeOH—$CHCl_3$ (10×25 mL). The organic layer was dried over $Na_2SO_4$, concentrated, and purified by silica gel column chromatography (MeOH—$CHCl_3$) to obtain Compound 4b.

6-(4-[(7H-pyrrolo[2,3-d]pyrimidin-4-yl)amino]phenoxy)-1-hexanol (Compound 4b). MS ($ESI^+$) m/z 327.4 $(M+H)^+$. $^1H$ NMR (400 MHz, DMSO-$d_6$) &I111.66 (bs, 1H), 9.13 (bs, 1H), 8.19 (s, 1H), 7.73-7.65 (m, 2H), 7.19-7.15 (m, 1H), 6.94-6.88 (m, 2H), 6.69-6.65 (m, 1H), 4.35 (t, J=4.8 Hz, 1H), 4.01 (t, J=6.4 Hz, 2H), 3.42-3.36 (m, 2H), 1.76-1.66 (m, 2H), 1.49-1.31 (m, 6H).

Step 4

To a solution of Compound 4b (55 mg, 0.11 mmol), R5-2C (45 mg, 0.105 mmol) and HOBt (30 mg, 0.2 mmol) in dry DMF (1 mL) was added triethylamine (20 mg, 0.2 mmol) and N-Ethyl-N'-(3-dimethylaminopropyl)carbodiimide hydrochloride (EDC-HCl) (40 mg, 0.2 mmol). The reaction mixture was stirred at room temperature for 18 hours. The reaction mixture was concentrated under vacuum, diluted with water (5 mL) and extracted with ethyl acetate (2×10 mL). The organic layer was dried over $Na_2SO_4$, concentrated and purified by preparative TLC (8% EtOH in $CHCl_3$) to obtain Ray06-003.

6-(4-(7H-pyrrolo[2,3-d]pyrimidin-4-ylamino)phenoxy)hexyl-2-(2-(2,6-dioxopiperidin-3-yl)-1,3-dioxoisoindolin-4-yloxy)acetate (Ray06-003). $^1H$ NMR ((400 MHz, DMSO-$d_6$) δ 11.67 (bs, 1H), 11.10 (s, 1H), 9.14 (bs, 1H), 8.19 (s, 1H), 7.79 (dd, J=7.2, 8.4 Hz, 1H), 7.72-7.64 (m, 2H), 7.49 (d, J=7.2 Hz, 1H), 7.42 (d, J=8.4 Hz, 1H), 7.19-7.16 (m, 1H), 6.94-6.89 (m, 2H), 6.69-6.66 (m, 1H), 5.15-5.06 (m, 3H), 4.15 (t, J=6.4 Hz, 2H), 3.93 (t, J=6.4 Hz, 2H), 2.95-2.82 (m, 1H), 2.71-2.56 (m, 2H), 2.07-2.00 (m, 1H), 1.73-1.57 (m, 4H), 1.46-1.31 (m, 4H). HPLC: to =5.47 min, 96.9%.

Example 4

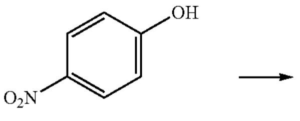

4-nitrophenol

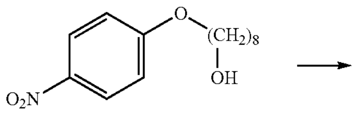

2c

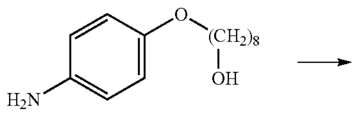

3c

-continued

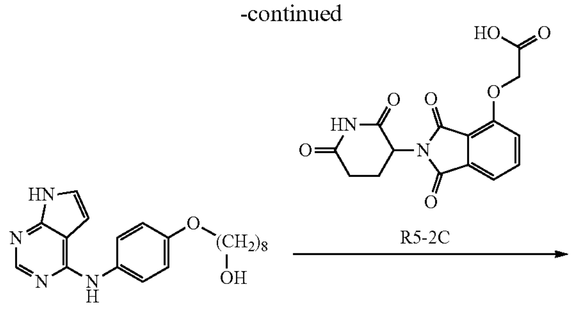

4c

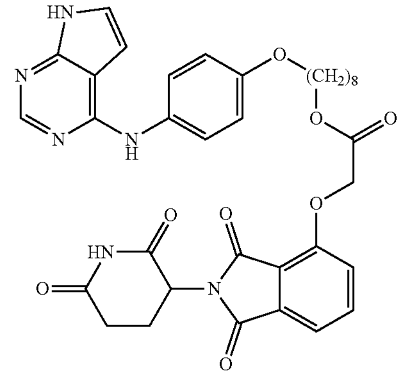

Ray06-004

Step 1

To a solution of 4-nitrophenol (1 eqv) and 8-bromo-1-octanol (1 eqv) in dry DMF (2.5 ml) was added $K_2CO_3$ (2 eqv). The reaction mixture was stir at 80° C. for 2 hours. The reaction mixture was concentrated, diluted with water (2 mL) and brine (8 mL), and extracted with $CHCl_3$ (3×30 mL). The organic layer was dried over $Na_2SO_4$, filtered, concentrated, and purified by silica gel column chromatography to obtain Compound 2c. 8-(4-Nitrophenoxy)-1-octanol (Compound 2c). $^1H$ NMR (400 MHz, $CDCl_3$) δ 8.23-8.17 (m, 2H), 6.96-6.91 (m, 2H), 4.04 (t, J=6.4 Hz, 2H), 3.65 (t, J=6.0 Hz, 2H), 1.88-1.78 (m, 2H), 1.62-1.56 (m, 2H), 1.52-1.44 (m, 2H), 1.42-1.34 (m, 6H).

Step 2

To a solution of Compound 2c (1 eqv) in 80% EtOH-water (5 mL) was add iron powder (6 eqv) and $CaCl_2$) (0.6 eqv). The reaction mixture was refluxed for 2 hours. The reaction mixture was cooled to ambient temperature and concentrated. The crude product was then diluted with water (5 mL) and extracted with ethyl acetate (2×10 mL). The organic layer was dried over $Na_2SO_4$, concentrated and purified by silica gel column chromatography to obtain Compound 3c. 8-(4-Aminophenoxy)-1-octanol (3c). $^1H$ NMR (500 MHz, $CDCl_3$) δ 6.76-6.72 (m, 2H), 6.66-6.62 (m, 2H), 3.87 (t, J=6.5 Hz, 2H), 3.64 (t, J=6.5 Hz, 2H), 3.55-3.35 (bs, 2H), 1.78-1.69 (m, 2H), 1.61-1.51 (m, 2H), 1.49-1.40 (m, 2H), 1.40-1.30 (m, 4H).

Step 3

A solution of 6-chloro-7-deazapurine (1 eqv) and Compound 3c (1 eqv) in ethylene glycol (2 mL) was heated at 120° C. and stirred for 3 hours. The reaction mixture was diluted with brine (20 mL) and extracted with 10% MeOH—$CHCl_3$ (10×25 mL). The organic layer was dried over $Na_2SO_4$, concentrated, and purified by silica gel column chromatography (MeOH—$CHCl_3$) to obtain Compound 4c.

8-(4-[(7H-pyrrolo[2,3-d]pyrimidin-4-yl)amino]phenoxy)-1-octanol (Compound 4c). $^1H$ NMR (400 MHz, DMSO-$d_6$) δ 11.66 (bs, 1H), 9.13 (bs, 1H), 8.19 (s, 1H), 7.72-7.67 (m, 2H), 7.19-7.16 (m, 1H), 6.93-6.89 (m, 2H), 6.69-6.66 (m, 1H), 4.35 (t, J=4.8 Hz, 1H), 3.94 (t, J=6.4 Hz, 2H), 3.41-3.35 (m, 2H), 1.75-1.64 (m, 2H), 1.44-1.38 (m, 4H), 1.36-1.24 (m, 6H).

Step 4

To a solution of Compound 4c (55 mg, 0.11 mmol), R5-2C (45 mg, 0.105 mmol) and HOBt (30 mg, 0.2 mmol) in dry DMF (1 mL) was added triethylamine (20 mg, 0.2 mmol) and N-Ethyl-N'-(3-dimethylaminopropyl)carbodiimide hydrochloride (EDC-HCl) (40 mg, 0.2 mmol). The reaction mixture was stirred at room temperature for 18 hours. The reaction mixture was concentrated under vacuum, diluted with water (5 mL) and extracted with ethyl acetate (2×10 mL). The organic layer was dried over $Na_2SO_4$, concentrated and purified by preparative TLC (8% EtOH in $CHCl_3$) to obtain Ray06-004.

8-(4-(7H-pyrrolo[2,3-d]pyrimidin-4-ylamino)phenoxy)octyl-2-(2-(2,6-dioxopiperidin-3-yl)-1,3-dioxoisoindolin-4-yloxy)acetate (Ray06-004). $^1H$ NMR (400 MHz, DMSO-$d_6$) δ□11.69 (bs, 1H), 11.10 (s, 1H), 9.16 (bs, 1H), 8.19 (s, 1H), 7.78 (t, J=8.0 Hz, 1H), 7.69 (d, J=9.0 Hz, 2H), 7.49 (d, J=7.0 Hz, 1H), 7.42 (d, J=8.0 Hz, 1H), 7.18 (s, 1H), 6.92 (d, J=9.0 Hz, 2H), 6.66 (s, 1H), 5.14-5.06 (m, 3H), 4.13 (t, J=6.5 Hz, 2H), 3.93 (t, J=6.5 Hz, 2H), 2.93-2.84 (m, 1H), 2.65-2.55 (m, 2H), 2.06-2.01 (m, 1H), 1.73-1.65 (m, 2H), 1.62-1.54 (m, 2H), 1.43-1.34 (m, 2H), 1.32-1.22 (m, 6H). HPLC: $t_R$=5.81 min, 98.0%.

Example 5

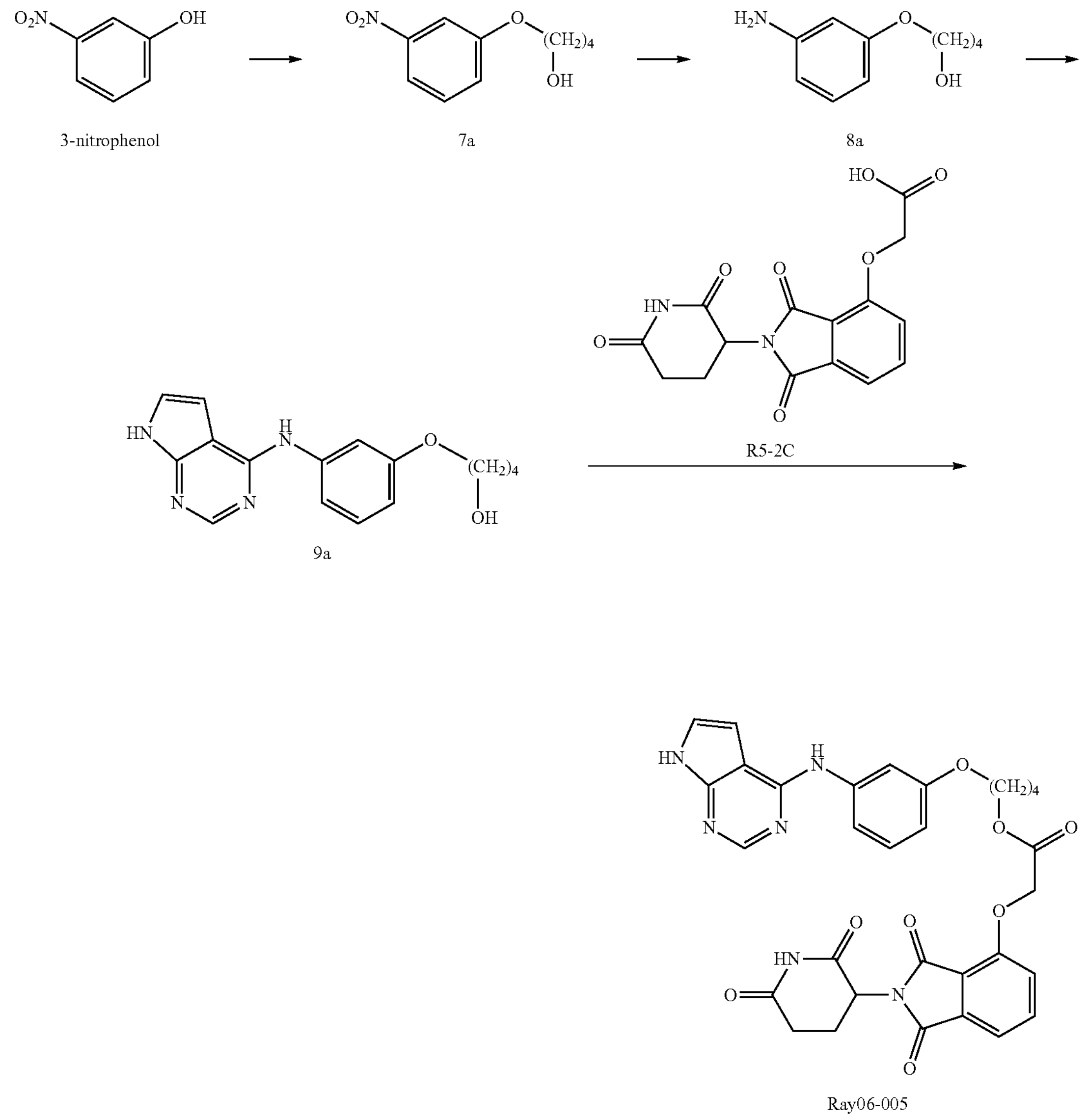

3-nitrophenol

7a

8a

R5-2C

9a

Ray06-005

Step 1

To a solution of 4-O-TBS-butyl-1-tosylate (1.30 mg, 4.6 mmol) and 3-nitrophenol (600 mg, 4.3 mmol) in dry dimethylformamide (DMF) (25 mL) was added $K_2CO_3$ (1.27 g, 9.2 mmol) and heated at 70° C. for 4 hours. The reaction mixture was concentrated, diluted with water (2 mL) and brine (8 mL) and extracted with $CHCl_3$ (3×30 mL). The organic layer was dried over $Na_2SO_4$, filtered, and concentrated. The crude material was dissolved in dry tetrahydrofuran (THF) (10 mL), cooled, and treated with 1M tetra-n-butylammonium fluoride (TBAF) in THE (5 ml, 5 mmol). The resulting mixture was stirred for 2 hours. The reaction mixture was concentrated, diluted with ethyl acetate (50 mL), and washed with water (2×10 mL) and brine (10 mL). The organic layer was dried over $Na_2SO_4$, filtered, concentrated, and purified by silica gel column chromatography to obtain Compound 7a.

4-(3-Nitrophenoxy)-1-butanol (Compound 7a). $^1$H NMR (400 MHz, $CDCl_3$) δ 7.84-7.80 (m, 1H), 7.72 (t, J=2.4 Hz, 1H), 7.42 (t, J=8.0 Hz, 1H), 7.24-7.20 (m, 1H), 4.09 (t, J=6.0 Hz, 2H), 3.75 (t, J=6.0 Hz, 2H), 1.99-1.91 (m, 2H), 1.82-1.74 (m, 2H).

Step 2

To a solution of Compound 7a (1 eqv) in 80% EtOH-water (5 mL) was add iron powder (6 eqv) and $CaCl_2$) (0.6 eqv). The reaction mixture was refluxed for 2 hours. The reaction mixture was cooled to ambient temperature and concentrated. The crude product was then diluted with water (5 mL) and extracted with ethyl acetate (2×10 mL). The organic layer was dried over $Na_2SO_4$, concentrated and purified by silica gel column chromatography to obtain Compound 8a.

4-(3-Aminophenoxy)-1-butanol (Compound 8a). $^1$H NMR (400 MHz, $CDCl_3$) δ 7.04 (t, J=8.0 Hz, 1H), 6.34-6.26 (m, 2H), 6.24 (t, J=2.4 Hz, 1H), 3.96 (t, J=6.0 Hz, 2H), 3.71 (t, J=6.0 Hz, 2H), 1.90-1.82 (m, 2H), 1.79-1.71 (m, 2H).

Step 3

A solution of 6-chloro-7-deazapurine (1 eqv) and Compound 8a (1 eqv) in ethylene glycol (2 mL) was heated at 120° C. and stirred for 3 hours. The reaction mixture was diluted with brine (20 mL) and extracted with 10% MeOH—$CHCl_3$ (10×25 mL). The organic layer was dried over $Na_2SO_4$, concentrated, and purified by silica gel column chromatography (MeOH—$CHCl_3$) to obtain Compound 9a.

4-(4-[(7H-pyrrolo[2,3-d]pyrimidin-4-yl)amino]phenoxy)-1-butanol (Compound 9a). $^1$H NMR (400 MHz, DMSO-$d_6$) δ 12.16 (bs, 1H), 10.00 (bs, 1H), 8.30 (s, 1H), 7.43 (s, 1H), 7.34-7.25 (m, 3H), 6.81 (s, 1H), 6.74 (s, 1H), 3.99 (t, J=6.4 Hz, 2H), 3.46 (t, J=6.4 Hz, 2H), 1.81-1.72 (m, 2H), 1.61-1.53 (m, 2H).

Step 4

To a solution of Compound 9a (55 mg, 0.11 mmol), R5-2C (45 mg, 0.105 mmol) and HOBt (30 mg, 0.2 mmol) in dry DMF (1 mL) was added triethylamine (20 mg, 0.2 mmol) and N-Ethyl-N'-(3-dimethylaminopropyl)carbodiimide hydrochloride (EDC-HCl) (40 mg, 0.2 mmol). The reaction mixture was stirred at room temperature for 18 hours. The reaction mixture was concentrated under vacuum, diluted with water (5 mL) and extracted with ethyl acetate (2×10 mL). The organic layer was dried over $Na_2SO_4$, concentrated and purified by preparative TLC (8% EtOH in $CHCl_3$) to obtain Ray06-005.

4-(3-(7H-pyrrolo[2,3-d]pyrimidin-4-ylamino)phenoxy)butyl-2-(2-(2,6-dioxopiperidin-3-yl)-1,3-dioxoisoindolin-4-yloxy)acetate (Ray06-005). $^1$H NMR (400 MHz, DMSO-$d_6$) δ 11.75 (bs, 1H), 11.11 (s, 1H), 9.23 (bs, 1H), 8.28 (s, 1H), 7.78 (dd, J=7.6, 8.8 Hz, 1H), 7.62 (t, J=2.4 Hz, 1H), 7.51-7.39 (m, 3H), 7.26-7.19 (m, 2H), 6.79 (dd, J=1.6, 3.2 Hz, 1H), 6.58 (dd, J=2.0, 8.0 Hz, 1H), 5.14-5.07 (m, 3H), 4.22 (t, J=6.4 Hz, 2H), 3.98 (t, J=6.4 Hz, 2H), 2.94-2.84 (m, 1H), 2.64-2.55 (m, 2H), 2.07-1.99 (m, 1H), 1.83-1.75 (m, 4H). HPLC: $t_R$=5.49 min, 98.0%.

Example 6

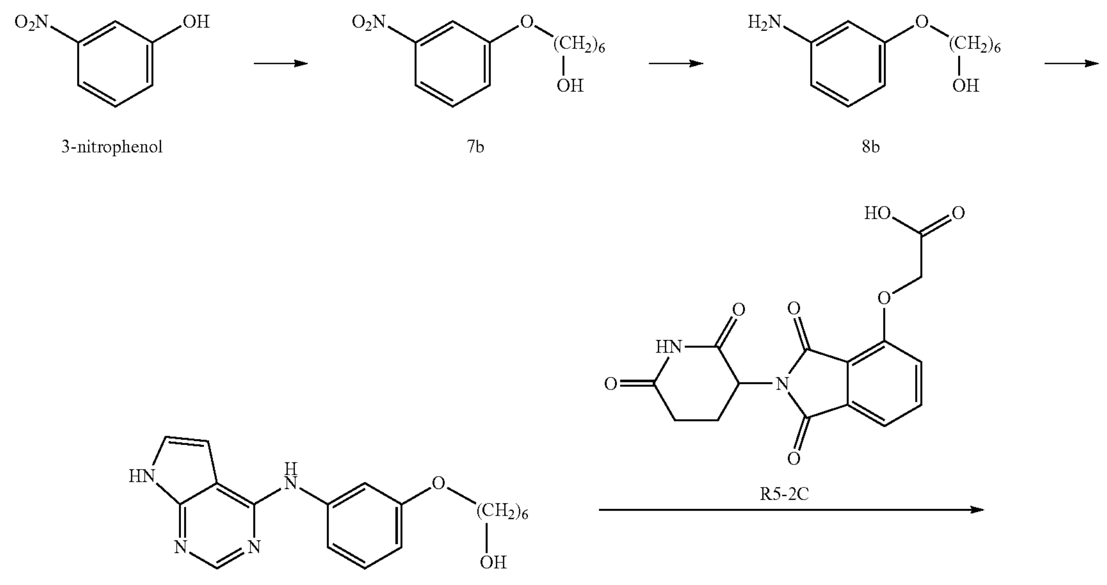

3-nitrophenol

7b

8b

R5-2C

9b

-continued

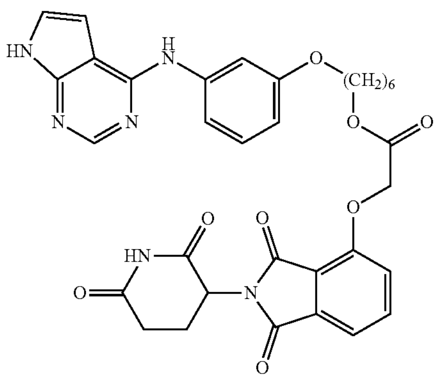

Ray06-006

Step 1

To a solution of 3-nitrophenol (1 eqv) and 6-bromo-1-hexanol (1 eqv) in dry DMF (2.5 ml) was added $K_2CO_3$ (2 eqv). The reaction mixture was stir at 80° C. for 2 hours. The reaction mixture was concentrated, diluted with water (2 mL) and brine (8 mL), and extracted with $CHCl_3$ (3×30 mL). The organic layer was dried over $Na_2SO_4$, filtered, concentrated, and purified by silica gel column chromatography to obtain Compound 7b. 6-(3-Nitrophenoxy)-1-hexanol (Compound 7b). 1H NMR (400 MHz, $CDCl_3$) δ 7.81 (ddd, J=0.8, 2.4, 8.0 Hz, 1H), 7.71 (t, J=2.4 Hz, 1H), 7.41 (t, J=8.0 Hz, 1H), 7.21 (ddd, J=0.8, 2.4, 8.4 Hz, 1H), 4.03 (t, J=6.4 Hz, 2H), 3.67 (t, J=6.4 Hz, 2H), 1.89-1.80 (m, 2H), 1.67-1.58 (m, 2H), 1.56-1.41 (m, 4H).

Step 2

To a solution of Compound 7b (1 eqv) in 80% EtOH-water (5 mL) was add iron powder (6 eqv) and $CaCl_2$) (0.6 eqv). The reaction mixture was refluxed for 2 hours. The reaction mixture was cooled to ambient temperature and concentrated. The crude product was then diluted with water (5 mL) and extracted with ethyl acetate (2×10 mL). The organic layer was dried over $Na_2SO_4$, concentrated and purified by silica gel column chromatography to obtain Compound 8b.

6-(3-Aminophenoxy)-1-hexanol (Compound 8b). $^1H$ NMR (400 MHz, $CDCl_3$) δ 7.04 (t, J=8.0) 6.34-6.23 (m, 3H), 3.91 (t, J=6.4 Hz, 2H), 3.67 (t, J=6.4 Hz, 2H), 1.82-1.74 (m, 2H), 1.65-1.56 (m, 2H), 1.53-1.42 (m, 4H).

Step 3

A solution of 6-chloro-7-deazapurine (1 eqv) and Compound 8b (1 eqv) in ethylene glycol (2 mL) was heated at 120° C. and stirred for 3 hours. The reaction mixture was diluted with brine (20 mL) and extracted with 10% MeOH—$CHCl_3$ (10×25 mL). The organic layer was dried over $Na_2SO_4$, concentrated, and purified by silica gel column chromatography (MeOH—$CHCl_3$) to obtain Compound 9b.

6-(4-[(7H-pyrrolo[2,3-d]pyrimidin-4-yl)amino]phenoxy)-1-hexanol (Compound 9b). $^1H$ NMR (400 MHz, DMSO-$d_6$) δ 12.04 (bs, 1H), 9.78 (bs, 1H), 8.29 (s, 1H), 7.48 (s, 1H), 7.38-7.24 (m, 3H), 6.80 (s, 1H), 6.70 (d, J=7.2 Hz, 1H), 3.97 (t, J=6.4 Hz, 2H), 1.78-1.68 (m, 2H), 1.50-1.32 (m, 6H).

Step 4

To a solution of Compound 9b (55 mg, 0.11 mmol), R5-2C (45 mg, 0.105 mmol) and HOBt (30 mg, 0.2 mmol) in dry DMF (1 mL) was added triethylamine (20 mg, 0.2 mmol) and N-Ethyl-N'-(3-dimethylaminopropyl)carbodiimide hydrochloride (EDC-HCl) (40 mg, 0.2 mmol). The reaction mixture was stirred at room temperature for 18 hours. The reaction mixture was concentrated under vacuum, diluted with water (5 mL) and extracted with ethyl acetate (2×10 mL). The organic layer was dried over $Na_2SO_4$, concentrated and purified by preparative TLC (8% EtOH in $CHCl_3$) to obtain Ray06-006.

6-(3-(7H-pyrrolo[2,3-d]pyrimidin-4-ylamino)phenoxy)hexyl-2-(2-(2,6-dioxopiperidin-3-yl)-1,3-dioxoisoindolin-4-yloxy)acetate (Ray06-006). $^1H$ NMR (400 MHz, DMSO-$d_6$) δ 11.76 (s, 1H), 11.10 (s, 1H), 9.26 (s, 1H), 8.28 (s, 1H), 7.78 (dd, J=7.2, 8.4 Hz, 1H), 7.6 (t, J=2.0 Hz, 1H), 7.50-7.39 (m, 3H), 7.25-7.18 (m, 2H), 6.81-6.77 (m, 1H), 6.59 (dd, J=2.4, 8.4 Hz, 1H), 5.14-5.06 (m, 3H), 4.15 (t, J=6.4 Hz, 2H), 3.95 (t, J=6.4 Hz, 2H), 2.94-2.84 (m, 1H), 2.63-2.52 (m, 2H), 2.07-2.00 (m, 1H), 1.76-1.68 (m, 2H), 1.62-1.55 (m, 2H), 1.48-1.32 (m, 4H). HPLC: $t_R$=5.73 min, 97.6%.

Example 7

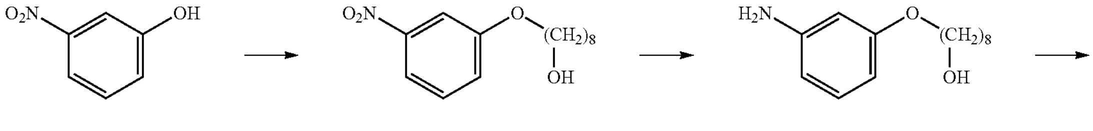

3-nitrophenol 7c 8c

-continued

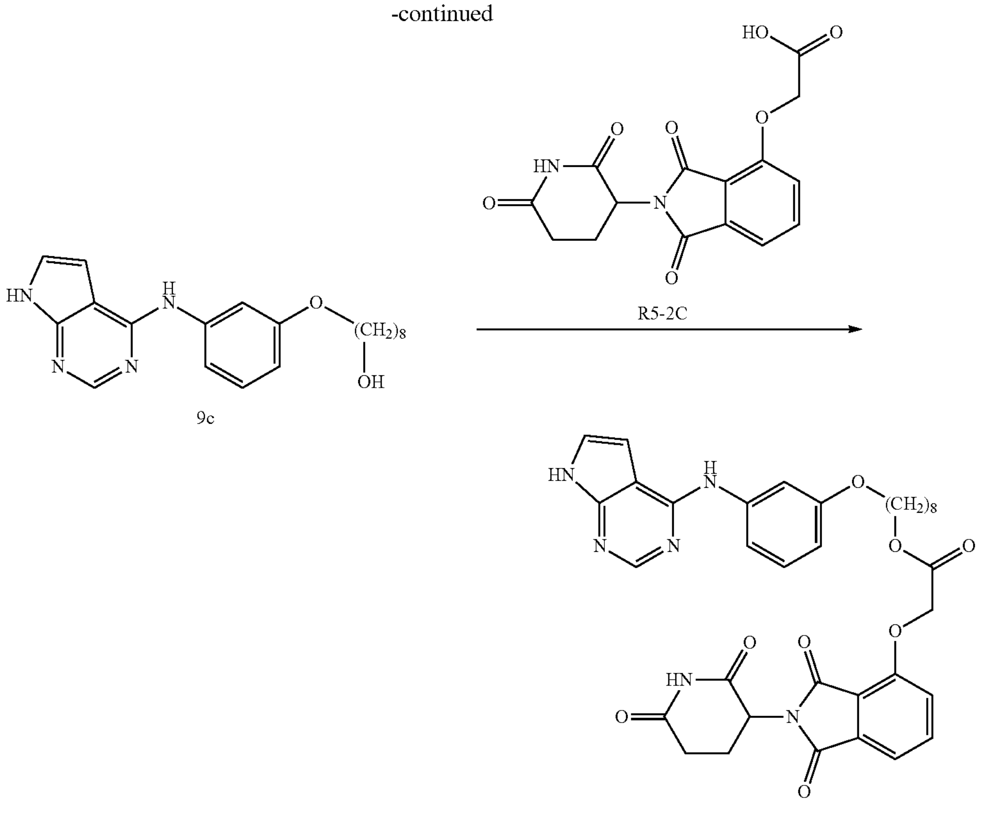

9c

Ray06-007

Step 1

To a solution of 3-nitrophenol (1 eqv) and 8-bromo-1-octanol (1 eqv) in dry DMF (2.5 ml) was added $K_2CO_3$ (2 eqv). The reaction mixture was stir at 80° C. for 2 hours. The reaction mixture was concentrated, diluted with water (2 mL) and brine (8 mL), and extracted with $CHCl_3$ (3×30 mL). The organic layer was dried over $Na_2SO_4$, filtered, concentrated, and purified by silica gel column chromatography to obtain Compound 7c. 8-(3-Nitrophenoxy)-1-octanol (Compound 7c). 1H NMR (400 MHz, $CDCl_3$) δ 7.81 (ddd, J=0.8, 2.4, 8.0 Hz, 1H), 7.71 (t, J=2.4 Hz, 1H), 7.41 (t, J=8.0 Hz, 1H), 7.21 (ddd, J=0.8, 2.4, 8.4 Hz, 1H), 4.03 (t, J=6.4 Hz, 2H), 3.67 (t, J=6.4 Hz, 2H), 1.89-1.80 (m, 2H), 1.67-1.58 (m, 2H), 1.56-1.41 (m, 8H).

Step 2

To a solution of Compound 7c (1 eqv) in 80% EtOH-water (5 mL) was add iron powder (6 eqv) and $CaCl_2$) (0.6 eqv). The reaction mixture was refluxed for 2 hours. The reaction mixture was cooled to ambient temperature and concentrated. The crude product was then diluted with water (5 mL) and extracted with ethyl acetate (2×10 mL). The organic layer was dried over $Na_2SO_4$, concentrated and purified by silica gel column chromatography to obtain Compound 8c.

8-(3-Aminophenoxy)-1-octanol (Compound 8c). $^1$H NMR (400 MHz, $CDCl_3$) δ 7.04 (t, J=16.0 Hz, 1H), 6.34-6.23 (m, 3H), 3.90 (t, J=6.8 Hz, 2H), 3.68-3.58 (m, 4H), 1.80-1.70 (m, 2H), 1.62-1.56 (m, 2H), 1.48-1.32 (m, 8H).

Step 3

A solution of 6-chloro-7-deazapurine (1 eqv) and Compound 8c (1 eqv) in ethylene glycol (2 mL) was heated at 120° C. and stirred for 3 hours. The reaction mixture was diluted with brine (20 mL) and extracted with 10% MeOH—$CHCl_3$ (10×25 mL). The organic layer was dried over $Na_2SO_4$, concentrated, and purified by silica gel column chromatography (MeOH—$CHCl_3$) to obtain Compound 9c.

8-(3-[(7H-pyrrolo[2,3-d]pyrimidin-4-yl)amino]phenoxy)-1-octanol (Compound 9c). $^1$H NMR (400 MHz, DMSO-$d_6$) δ 12.11 (bs, 1H), 9.89 (bs, 1H), 8.29 (s, 1H), 7.46 (s, 1H), 7.37-7.25 (m, 3H), 6.81 (s, 1H), 6.72 (d, J=7.2 Hz, 1H), 3.97 (t, J=6.4 Hz, 2H), 3.37 (t, J=6.4 Hz, 2H), 1.78-1.68 (m, 2H), 1.47-1.27 (m, 10H).

Step 4

To a solution of Compound 9c (55 mg, 0.11 mmol), R5-2C (45 mg, 0.105 mmol) and HOBt (30 mg, 0.2 mmol) in dry DMF (1 mL) was added triethylamine (20 mg, 0.2 mmol) and N-Ethyl-N'-(3-dimethylaminopropyl)carbodiimide hydrochloride (EDC-HCl) (40 mg, 0.2 mmol). The reaction mixture was stirred at room temperature for 18 hours. The reaction mixture was concentrated under vacuum, diluted with water (5 mL) and extracted with ethyl acetate (2×10 mL). The organic layer was dried over $Na_2SO_4$, concentrated and purified by preparative TLC (8% EtOH in $CHCl_3$) to obtain Ray06-007.

8-(3-(7H-pyrrolo[2,3-d]pyrimidin-4-ylamino)phenoxy)octyl-2-(2-(2,6-dioxopiperidin-3-yl)-1,3-dioxoisoindolin-4-yloxy)acetate (Ray06-007). $^1$H NMR (500 MHz, DMSO-$d_6$)

δ 11.75 (s, 1H), 11.11 (s, 1H), 9.22 (s, 1H), 8.31 (d, J=15.5 Hz, 1H), 7.81-7.76 (m, 1H), 7.64-7.61 (m, 1H), 7.50-7.39 (m, 3H), 7.25-7.18 (m, 2H), 6.80-6.78 (m, 1H), 6.58 (dd, J=2.0, 7.5 Hz, 1H), 5.13-5.08 (m, 3H), 4.12 (t, J=7.0 Hz, 2H), 3.95 (t, J=7.0 Hz, 2H), 2.94-2.84 (m, 1H), 2.63-2.52 (m, 2H), 2.07-2.00 (m, 1H), 1.76-1.68 (m, 2H), 1.62-1.55 (m, 2H), 1.44-137 (m, 2H), 1.35-1.25 (m, 6H). HPLC: $t_R$=6.15 min, 97.3%.

Example A

Of the series of novel compositions designed, synthesized, and tested, the TTBK1 degrader Ray06-006 showed the strongest dose-dependent effect on TTBK1 protein levels with IC50 of 0.05-0.2 μM. Regarding tau, a reduction in total tau was observed with a strong dose-dependent effect in the A152T tauopathy model. There was also a reduction in P-tau across all epitopes tested, whether TTBK1-dependent (AT8, S422) or not (S396). Analysis of P-tau/total tau in A152T suggests that the reduction in tau phosphorylation and in total tau levels is very similar, except for S396 P-tau (non-TTBK1 site). For the P301L neurons, reduction in tau phosphorylation seems to be even more accentuated that the effect on total tau. Overall, the results indicate that reduction in P-tau occurs in parallel to a reduction in total tau, possibly due to changes in tau oligomerization and degradation propensity. Results are shown in FIGS. 2, 3, and 6-12.

Example B

Human NPC Lines and Post-Mortem Human Brain Samples

Reprogramming of patient dermal fibroblasts into iPSCs by non-integrating methods and subsequent conversion into cortical-enriched neural progenitor cells were previously described (Silva M C, Cheng C, Mair W, Almeida S, Fong H, Biswas M H U, Zhang Z, Huang Y, Temple S, Coppola G, Geschwind D H, Karydas A, Miller B L, Kosik K S, Gao F B, Steen J A, Haggarty S J. Human iPSC-Derived Neuronal Model of Tau-A152T Frontotemporal Dementia Reveals Tau-Mediated Mechanisms of Neuronal Vulnerability. Stem Cell Reports. 2016 Sep. 13; 7(3):325-340; Seo J, Kritskiy O, Watson L A, Barker S J, Dey D, Raja W K, Lin Y T, Ko T, Cho S, Penney J, Silva M C, Sheridan S D, Lucente D, Gusella J F, Dickerson B C, Haggarty S J, Tsai L H. Inhibition of p25/Cdk5 Attenuates Tauopathy in Mouse and iPSC Models of Frontotemporal Dementia. J Neurosci. 2017 Oct. 11; 37(41):9917-9924). The cell lines employed in this work were as follows: NPC line FTD19-L5-RC6 (Silva et al., 2016) was derived from a male individual with Progressive Supranuclear Palsy (PSP) carrying the risk variant tau-A152T (c. 1407G>A, rs 143624519); NPC line MGH2046-RC1 (Seo et al., 2017; Silva et al., 2019) was derived from a female individual with FTD carrying the autosomal dominant mutation tau-P301L (c.$C_{1907}$T, r563751273); NPC Control-1 or 8330-8-RC1 (Sheridan et al., 2011; Silva et al., 2016) was derived from an unaffected male individual (tau wild type (WT)); and NPC Control-2 or MGH2069-RC1 (Seo et al., 2017; Silva et al., 2019) was derived from an unaffected female individual (tau-WT). Post-mortem human brain samples from healthy controls and A152T (PSP) and P301L(FTD) for comparison were generously provided from the University of California San Francisco (UCSF) Memory & Aging Center.

NPC Culture, Differentiation and Compound Treatment

NPCs were cultured in 6-well (Fisher Scientific Corning) or 96-well flat bottom (Fisher Scientific Corning) plates coated with poly-ornithine (20 μg/mL in water, Sigma) and laminin (5 μg/mL in PBS, Sigma), referred to as POL-coated plates. Culture medium was DMEM/F12-B27 [70% DMEM (Gibco), 30% Ham's-F12 (Fisher Scientific Corning), 2% B27 (Gibco), 1% penicillin-streptomycin (Gibco)], supplemented with EGF (20 ng/mL, Sigma), FGF (20 ng/mL, Stemgent) and heparin (5 μg/mL, Sigma) for NPC proliferation. For NPC differentiation over the course of several weeks (six to eight weeks, experiment-dependent), cells were plated at an average density of 75,000 cells/$cm^2$ and growth factors were omitted from the medium, which was exchanged twice per week (Silva et al., 2016). Compound treatment in 6-well plate format was performed in 2 mL medium volume by removing 1 mL of conditioned medium from the culture and adding 1 mL of new medium pre-mixed with the compound at the appropriate 2× concentration, followed by incubation at 37° C. for the designated time. Compound treatment in 96-well plates was performed in 100 μL medium by adding compound directly to each well, followed by incubation at 37° C. As a control, neurons were also treated with vehicle alone, i.e., dimethyl sulfoxide (DMSO) at 0.1% v/v, and this corresponds to 0 μM degrader treatment in FIGS. 6-12. Compounds were kept as 10 mM stock concentrations and serial dilutions were prepared before each experiment in 10-fold dilutions so that the same volume (and % DMSO) was added per well of cells, independent of degrader final concentration.

Western Blot Analysis

NPCs were differentiated in 6-well plates at an average density of 75,000 cells/$cm^2$. Neurons were washed in DPBS (Corning), lifted into suspension by scrapping, transferred to eppendorf tubes, and spun down at 3,000 xg for 5 min. Cell pellets were lysed in RIPA buffer (Boston Bio-Products) supplemented with 2% SDS (Sigma), 1% Halt Protease/Phosphatase inhibitors (Thermo Fisher Scientific), 1:5000 Benzonase (Sigma), and 10 mM DTT (New England BioLabs), for 15 min at room temperature. Lysates were centrifugated at 20,000×g for 20 min and the supernatants were transferred to new eppendorf tubes for analysis. For post-mortem human brain lysates, tissue samples (~20-30 mg chunks) were resuspended in 10× volume of the weight of tissue with RIPA buffer (same composition as above) and homogenized thoroughly with a handheld motor grinder (VWR), to promote tissue disintegration, holding the tube over dry-ice. Samples were incubated with constant agitation on an orbital shaker for 1 hour at 4° C. Samples were then centrifuged for 20 min at 26,000 Xg at 4° C. in a microcentrifuge and the supernatants were transferred to new ice-cold Eppendorf tubes with the pellet discarded. Protein concentration quantification was performed using the Pierce BCA Protein Assay kit (ThermoFisher Scientific). For western blot, 10 μg of total protein per well and in SDS blue loading buffer (New England Biolabs), were analyzed by SDS-PAGE. Alternatively, cell lysis was performed directly in 8× the cell pellet volume with SDS sample loading buffer (New England Biolabs) and boiled for 15 min prior to SDS-PAGE. Electrophoresis was performed with the Novex NuPAGE SDS-PAGE Gel System (Invitrogen). Proteins were transferred from the gel onto PVDF membranes (EMD Millipore) using standard procedures. Membranes were blocked in 5% BSA (Sigma) in Tris-buffered saline with Tween-20 (TBST, Boston Bio-Products), incubated overnight with primary antibody in 5% BSA-TBST at 4° C., followed by incubation with the corresponding HRP-linked secondary antibody at 1:4000 dilution (Cell Signaling Technology). The antibodies used were as follows: TTBK1 (Millipore ABN348), total tau TAU5 (Invitrogen AHB0042), total non-phosphorylated tau TAU1 (clone PC1C6 Millipore MAB3420), P-tau Ser396 (Invitrogen 44752G), P-tau Ser422 (GeneTex GTX86147), P-tau AT8 (Thermo Scientific MN1020)) and 3-ACTIN (Sigma A1978). Blots were developed with SuperSignal West Pico Chemiluminescent Substrate (ThermoFisher) according to manufacturer's instructions, exposed to autoradiographic films (LabScientific by ThermoFisher), and scanned on an Epson Perfection V800 Photo Scanner. Protein bands' densitometry (pixel mean intensity in arbitrary units, a.u.) was measured with Adobe Photoshop 2021 (v.22.4.3) Histogram function and normalized to the respective internal control (β-ACTIN) band. Calculations were performed in Microsoft Excel (v.16.52), and graphs were plotted in GraphPad Prism 9 (v.9.2.0).

Statistical Information

Graphed data represent mean values±SD (standard deviation) or ±SEM (standard error of the mean), calculated using Microsoft Excel and GraphPad Prism. P-value<0.05 was considered the threshold for statistical significance. P-value significance intervals (*) are provided within each figure legend, together with the statistical test performed for each experiment. N values are indicated within figure legends and refer to biological replicates (NPC differentiation cultures independent setup and analysis, at different times), whereas technical replicates refer to the repeated analysis of the same samples. Derived statistics correspond to analysis of averaged values across biological replicates.

OTHER EMBODIMENTS

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:

1. A compound of Formula (I):

(I)

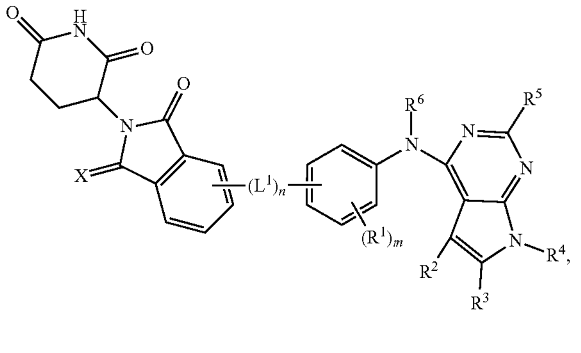

or a pharmaceutically acceptable salt thereof, wherein:

n is an integer selected from 1 to 10;

each $L^1$ is independently selected from C(=O), $N(R^N)$, S, S(=O), $S(=O)_2$, O, $(-C_{1-3}$ alkylene-O$-)_x$, $(-O-C_{1-3}$ alkylene-$)_x$, $C_{1-10}$ alkylene, $C_{2-6}$ alkenylene, $C_{2-6}$ alkynylene, $C_{3-10}$ cycloalkylene, $C_{6-10}$ arylene, 5-14 membered heteroarylene, and 4-10 membered heterocycloalkylene, wherein each x is independently an integer from 1 to 10 and each $C_{1-10}$ alkylene, $C_{2-6}$ alkenylene, $C_{2-6}$ alkynylene, $C_{3-10}$ cycloalkylene, $C_{6-10}$ arylene, 5-14 membered heteroarylene, and 4-10 membered heterocycloalkylene is optionally substituted with 1, 2, or 3 substituents independently selected from OH, $NO_2$, CN, halo, amino, and carboxy;

each $R^N$ is independently selected from H, $C_{1-3}$ alkyl, and $C_{1-3}$ haloalkyl;

X is O, or X is absent;

m is an integer from 0 to 4;

each $R^1$ is independently selected from halo, $C_{1-3}$ alkyl, $C_{1-3}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl;

each $R^2$, $R^3$, and $R^5$ is independently selected from H, halo, $C_{1-3}$ alkyl, $C_{1-4}$ haloalkyl, $C_{1-3}$ alkoxy, $C_{1-3}$ haloalkoxy, OH, $NO_2$, CN, halo, amino, $C_{1-3}$ alkylamino, di($C_{1-3}$ alkyl)amino, carboxy, and $C_{1-3}$ alkoxycarbonyl; and $R^4$ and $R^6$ are independently selected from H, $C_{1-3}$ alkyl, and $C_{1-3}$ haloalkyl.

2. The compound of claim 1, wherein X is O.

3. The compound of claim 1, wherein X is absent.

4. The compound of claim 1, wherein the compound of Formula (I) has formula:

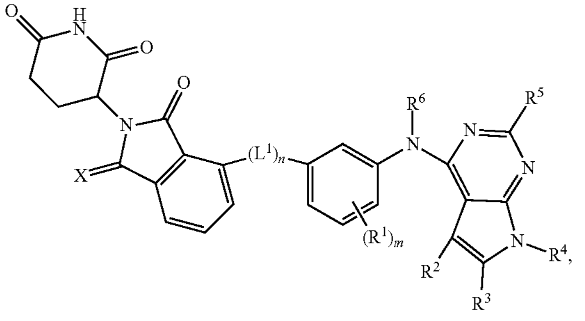

or a pharmaceutically acceptable salt thereof.

5. The compound of claim 1, wherein the compound of Formula (I) has formula:

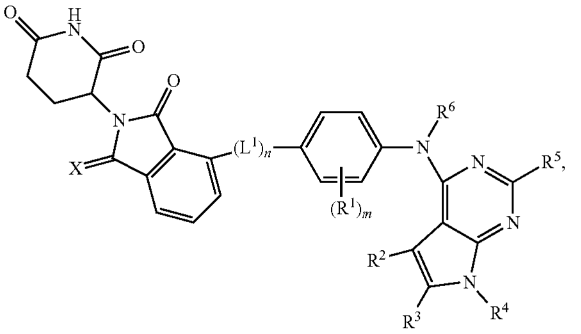

or a pharmaceutically acceptable salt thereof.

6. The compound of claim 1, wherein the compound of Formula (I) has formula:

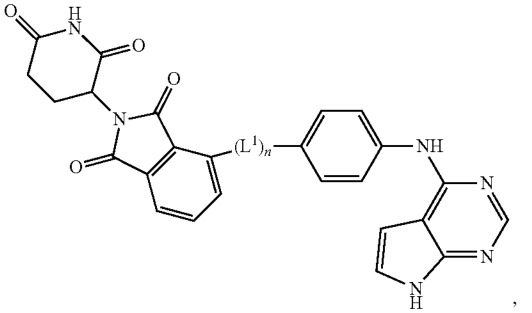

or a pharmaceutically acceptable salt thereof.

7. The compound of claim 1, wherein the compound of Formula (I) has formula:

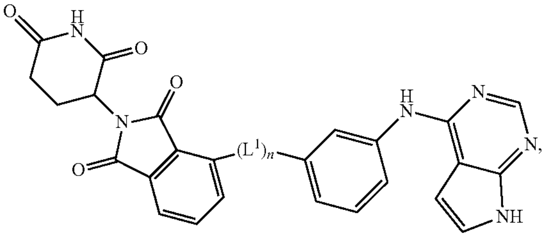

or a pharmaceutically acceptable salt thereof.

8. The compound of claim 1, wherein n is an integer from 3 to 8.

9. The compound of claim 8, wherein n is 6.

10. The compound of claim 1, wherein each $L^1$ is independently selected from C(=O), NH, O, and $C_{1-10}$ alkylene.

11. The compound of claim 1, wherein each $L^1$ is independently selected from C(=O), O, and $C_{1-10}$ alkylene.

12. The compound of claim 1, wherein the compound of Formula (I) has formula:

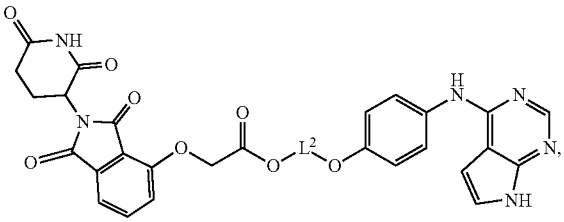

or a pharmaceutically acceptable salt thereof, wherein: $L^2$ is $C_{1-10}$ alkylene.

13. The compound of claim 1, wherein the compound of Formula (I) has formula:

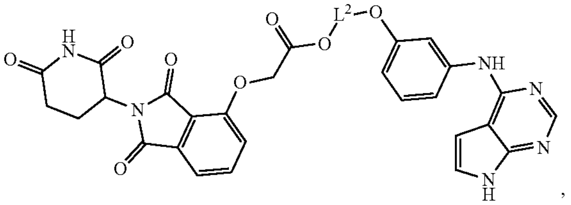

or a pharmaceutically acceptable salt thereof, wherein: $L^2$ is $C_{1-10}$ alkylene.

14. The compound of claim 12, wherein $L^2$ is butylene, hexylene, or octylene.

15. The compound of claim 13, wherein $L^2$ is butylene, hexylene, or octylene.

16. The compound of claim 1, wherein the compound of Formula (I) is selected from any one of the following compounds:

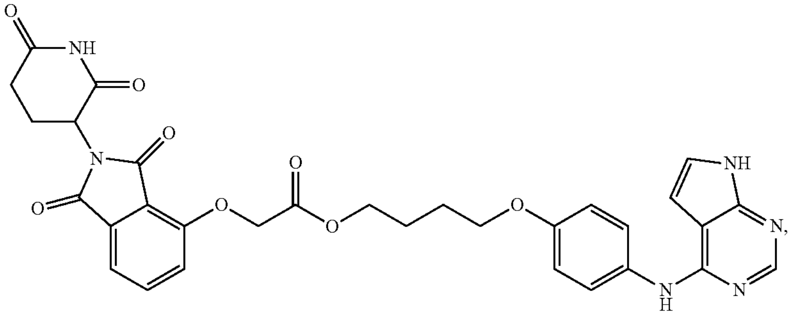

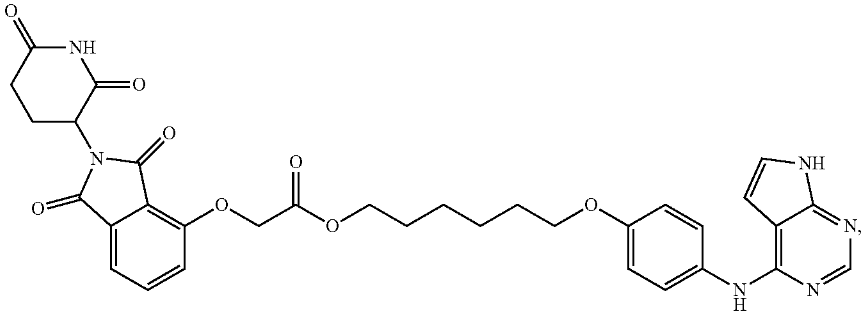

-continued

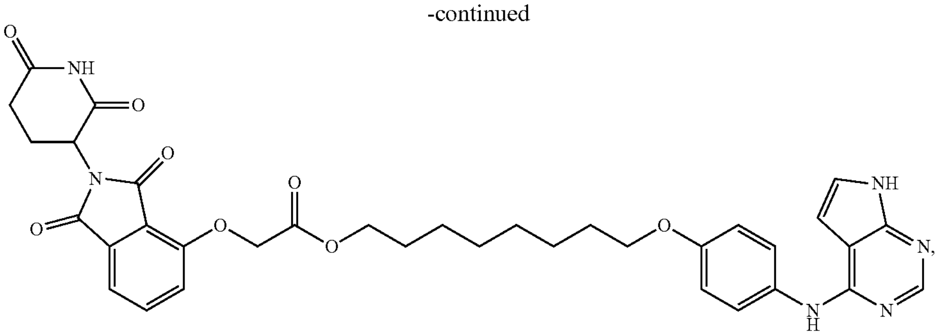

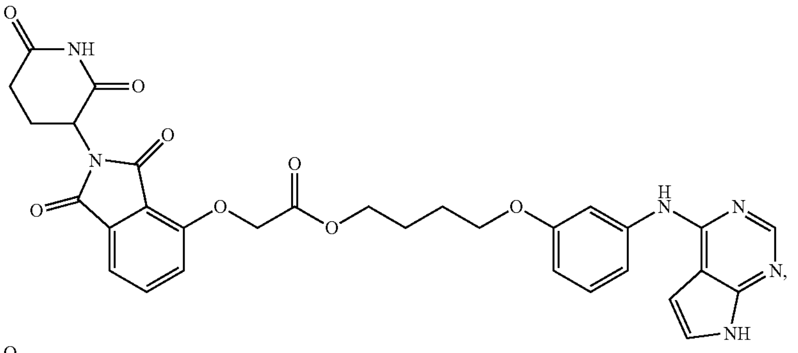

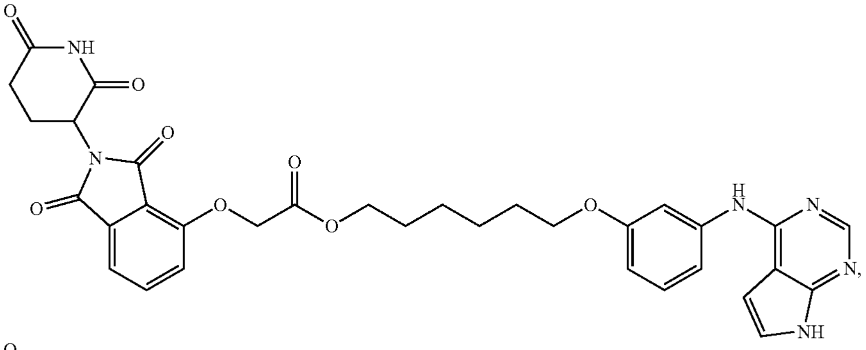

and

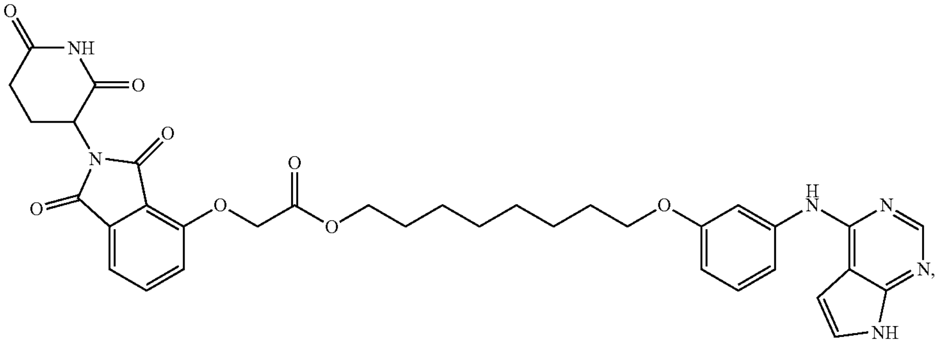

or a pharmaceutically acceptable salt thereof.

17. A pharmaceutical composition comprising the compound of claim 1, or a pharmaceutically acceptable salt thereof, and a pharmaceutically acceptable carrier.

18. A method of treating a neurodegenerative disease or disorder selected from tauopathy, Alzheimer's disease, frontotemporal dementia, amyotrophic lateral sclerosis, multiple sclerosis, frontotemporal lobar degeneration with tau pathology, Huntington's disease, and Parkinson's disease, the method comprising administering to the subject in need thereof a therapeutically effective amount of the compound of claim 1, or a pharmaceutically acceptable salt thereof.

19. The method of claim 18, wherein the tauopathy is selected from Primary age-related tauopathy (PART), Chronic traumatic encephalopathy (CTE), Progressive supranuclear palsy (PSP), Corticobasal degeneration (CBD), Frontotemporal dementia and parkinsonism linked to chromosome 17 (FTDP-17), Lytico-bodig disease, Ganglioglioma and gangliocytoma, Meningioangiomatosis, Postencephalitic parkinsonism, Subacute sclerosing panencephalitis (SSPE), Argyrophilic grain disease (AGD), lead encephalopathy, tuberous sclerosis, pantothenate kinase-associated neurodegeneration, and lipofuscinosis, and Pick's disease.

20. The method of claim 18, wherein the neurodegenerative disease or disorder is Alzheimer's disease.

21. The method of claim 18, wherein the neurodegenerative disease or disorder is frontotemporal dementia.

22. The method of claim 19, wherein the tauopathy is progressive supranuclear palsy.

* * * * *